(12) United States Patent
Smyczynski

(10) Patent No.: US 10,973,974 B2
(45) Date of Patent: *Apr. 13, 2021

(54) EXTRACORPOREAL PHOTODYNAMIC BLOOD ILLUMINATION (IRRADIATION) FOR THE TREATMENT OF CARBON MONOXIDE POISONING

(71) Applicant: Mark S. Smyczynski, Jefferson, MA (US)

(72) Inventor: Mark S. Smyczynski, Jefferson, MA (US)

( * ) Notice: Subject to any disclaimer, the term of this patent is extended or adjusted under 35 U.S.C. 154(b) by 167 days.

This patent is subject to a terminal disclaimer.

(21) Appl. No.: 16/042,601

(22) Filed: Jul. 23, 2018

(65) Prior Publication Data

US 2019/0269843 A1 Sep. 5, 2019

Related U.S. Application Data

(63) Continuation of application No. 15/853,848, filed on Dec. 24, 2017, which is a continuation of application No. 14/513,670, filed on Oct. 14, 2014, now abandoned, which is a continuation of application No. 13/372,380, filed on Feb. 13, 2012, now Pat. No. 8,858,880.

(60) Provisional application No. 61/442,211, filed on Feb. 12, 2011.

(51) Int. Cl.
*A61M 1/36* (2006.01)
*A61M 1/32* (2006.01)

(52) U.S. Cl.
CPC ............ *A61M 1/3681* (2013.01); *A61M 1/32* (2013.01); *A61M 1/3659* (2014.02); *A61M 1/3683* (2014.02); *A61M 2202/0233* (2013.01); *A61M 2205/3606* (2013.01)

(58) Field of Classification Search
CPC .............. A61M 1/3681; A61M 1/3659; A61M 1/3683; A61M 1/32; A61M 2202/0233; A61M 2205/3606
USPC ......................................................... 422/45
See application file for complete search history.

(56) References Cited

U.S. PATENT DOCUMENTS

| | | | | |
|---|---|---|---|---|
| 5,862,449 | A * | 1/1999 | Bischoff | C02F 1/325 422/186.3 |
| 7,601,201 | B2 * | 10/2009 | Fukutomi | B01D 19/0005 95/46 |
| 2005/0040029 | A1 * | 2/2005 | Monzyk | A61M 1/32 204/157.15 |

(Continued)

*Primary Examiner* — Andrew J Mensh
(74) *Attorney, Agent, or Firm* — Armis IP Law, LLC

(57) ABSTRACT

Treatment of carbon monoxide poisoning of a body by removal of a portion of the blood from the body, placing the portion in an exposure cell, exposing the portion in the cell to light of wave length and intensity that causes dissociation of carbon monoxide from hemoglobin, and returning the portion to the body. The intensity and wave length of the light is sufficient to dissociate a therapeutically-effective amount of carbon monoxide from the hemoglobin in the blood. The blood is circulated from and to the body through a concentric double lumen cannula. The wave lengths of the light are 540 and/or 570 nanometers. The cell exposes the blood to at least 9.5 Joules of dissociative light per milliliter of blood, and least 9.5 Watts of dissociative light per milliliter of blood per second. Oxygen is provided to, and the dissociated carbon monoxide is removed from the system.

17 Claims, 32 Drawing Sheets

(56) References Cited

U.S. PATENT DOCUMENTS

2008/0147012 A1\* 6/2008 Rome ............... A61M 25/0097
604/167.04

\* cited by examiner

WATTAGE CALCULATION REQUIRED

FOR

EXTRACORPOREAL

SUSTAINED

PHOTOLYSIS

FIG. 2

TRUE EQUATION $$\frac{I}{I_0} = e^{-\rho\sigma d} + \frac{q_\alpha}{q}\left[e^{-\rho\sigma d + qd} - e^{-\rho\sigma d}\right]$$

WHERE $\sigma = \sigma_a + \sigma_s$

FOR NONABSORBING SCATTERERS $q = \rho\sigma_s$ $$\frac{I}{I_0} = e^{-\rho\sigma_a d}\left[e^{-\rho\sigma_s d} + \frac{q_\alpha}{q}\left(1 - e^{-\rho\sigma_s d}\right)\right]$$

FIG. 3

$$\frac{I}{I_0} = e^{-\rho\sigma_a d}\left[e^{-\rho\sigma_s d} + \frac{q_\alpha}{q}\left(1-e^{-\rho\sigma_s d}\right)\right]$$

$$\ln\frac{I}{I_0} = \ln\left\{e^{-\rho\sigma_a d}\left[e^{-\rho\sigma_s d} + \frac{q_\alpha}{q}\left(1-e^{-\rho\sigma_s d}\right)\right]\right\}$$

$$\ln\frac{I}{I_0} = \ln e^{-\rho\sigma_a d} + \ln\left[e^{-\rho\sigma_s d} + \frac{q_\alpha}{q}\left(1-e^{-\rho\sigma_s d}\right)\right]$$

$$\ln\frac{I}{I_0} = -\rho\sigma_a d + \ln\left[e^{-\rho\sigma_s d} + \frac{q_\alpha}{q}\left(1-e^{-\rho\sigma_s d}\right)\right]$$

$$-\ln\frac{I}{I_0} = \rho\sigma_a d - \ln\left[e^{-\rho\sigma_s d} + \frac{q_\alpha}{q}\left(1-e^{-\rho\sigma_s d}\right)\right]$$

$$\ln\left(\frac{I}{I_0}\right)^{-1} = \rho\sigma_a d - \ln\left[e^{-\rho\sigma_s d} + \frac{q_\alpha}{q}\left(1-e^{-\rho\sigma_s d}\right)\right]$$

$$\ln\frac{I_0}{I} = \rho\sigma_a d - \ln\left[e^{-\rho\sigma_s d} + \frac{q_\alpha}{q}\left(1-e^{-\rho\sigma_s d}\right)\right]$$

FIG. 4

$$\frac{I}{I_o} = e^{-\rho\sigma_a d}\left[e^{-\rho\sigma_s d} + \frac{q_\alpha}{q}\left(1 - e^{-\rho\sigma_s d}\right)\right]$$

$$\log\frac{I}{I_o} = \log\left\{e^{-\rho\sigma_a d}\left[e^{-\rho\sigma_s d} + \frac{q_\alpha}{q}\left(1 - e^{-\rho\sigma_s d}\right)\right]\right\}$$

$$\log\frac{I}{I_o} = \log e^{-\rho\sigma_a d} + \log\left[e^{-\rho\sigma_s d} + \frac{q_\alpha}{q}\left(1 - e^{-\rho\sigma_s d}\right)\right]$$

$$\log\frac{I}{I_o} = (0.434)(-\rho\sigma_a d) + \log\left[e^{-\rho\sigma_s d} + \frac{q_\alpha}{q}\left(1 - e^{-\rho\sigma_s d}\right)\right]$$

$$\log\frac{I}{I_o} = -(0.434)(\rho\sigma_a d) + \log\left[e^{-\rho\sigma_s d} + \frac{q_\alpha}{q}\left(1 - e^{-\rho\sigma_s d}\right)\right]$$

$$-\log\frac{I}{I_o} = (0.434)(\rho\sigma_a d) - \log\left[e^{-\rho\sigma_s d} + \frac{q_\alpha}{q}\left(1 - e^{-\rho\sigma_s d}\right)\right]$$

$$\log\left(\frac{I}{I_o}\right)^{-1} = (0.434)(\rho\sigma_a d) - \log\left[e^{-\rho\sigma_s d} + \frac{q_\alpha}{q}\left(1 - e^{-\rho\sigma_s d}\right)\right]$$

$$\log\frac{I_o}{I} = (0.434)(\rho\sigma_a d) - \log\left[e^{-\rho\sigma_s d} + \frac{q_\alpha}{q}\left(1 - e^{-\rho\sigma_s d}\right)\right]$$

$$OD = (0.434)(\rho\sigma_a d) - \log\left[e^{-\rho\sigma_s d} + \frac{q_\alpha}{q}\left(1 - e^{-\rho\sigma_s d}\right)\right]$$

FIG. 5

At 540nm incident photons $\sigma_a$ and $\sigma_s$ are related such that $\sigma_a$ is a maximum and $\sigma_s$ is a minimum, and $$\ln \frac{I}{I_0} = \ln e^{-\rho \sigma_a d} + \ln \left[ e^{-\rho \sigma_s d} + \frac{q_a}{q} \left( 1 - e^{-\rho \sigma_s d} \right) \right]$$

can be approximated in the 540nm region by $$\ln \frac{I}{I_0} = \ln e^{-\rho \sigma_a d}$$

$$\ln \frac{I}{I_0} = -\rho \sigma_a d$$

$$e^{\ln \frac{I}{I_0}} = e^{-\rho \sigma_a d}$$

$$\frac{I}{I_0} = e^{-\rho \sigma_a d}$$

FIG. 6

FOR HUMAN BLOOD $\rho \leftrightarrow [HgB]$ IN $mM/L = 9\ mM/L$ $\sigma_a \leftrightarrow \epsilon_{HgB}$ IN $L/mMcm = 15.5\ L/mMcm$ AT $540nm$ $d \leftrightarrow x$ IN $cm = x\ cm$ $\dfrac{I}{I_o} = e^{-\rho \sigma_a d} \leftrightarrow \dfrac{I}{I_o} = e^{-[HgB]\epsilon_{HgB} x}$ $[HgB]\epsilon_{HgB} = (9\ \cancel{mM/L})(15.5\ \cancel{L/mMcm}) = 139.5/cm$ AT $x = 0.01 cm$ $\dfrac{I}{I_o} = e^{-(139.5/cm)(0.01 cm)}$

FIG. 7

$\dfrac{I}{I_o} = e^{-1.395} = 0.2478 \cong 0.25$

AT $x = 0.013 cm$ $\dfrac{I}{I_o} = e^{-(139.5/cm)(0.013 cm)} = e^{-1.8135} = 0.16$ What is the volume of a thin disc of fluid 10cm in diameter and 0.01cm thick $A = \pi (5cm^2) = 78.54 cm^2$ $V = (78.54 cm^2)(0.01 cm) = 0.7854 cm^3$ And for a diameter of 10cm and thickness of 0.013cm $V = (78.54 cm^2)(0.013 cm) = 1.02 cm^3 \cong 1 cm^3$ Assume $1 cm^3$ of whole blood $= 1 mL$ Number of HgB molecules in 1mL of blood $\left(9 \frac{\cancel{mM}}{\cancel{L}}\right)\left(\frac{1 \cancel{L}}{10^3 \cancel{mL}}\right)\left(\frac{1 \cancel{mL}}{1}\right)\left(\frac{1 \cancel{M}}{10^3 \cancel{mM}}\right)\left(\frac{6.023 \times 10^{23}}{\cancel{M}}\right)$ $= \frac{(9)(6.023)}{1} \times 10^{23} \times 10^{-6}$ $= 54.21 \times 10^{17} = 5.421 \times 10^{18}$ No. of HgB / 1mL

FIG. 8

$$E = h\nu = \frac{hc}{\lambda}$$

$$= \frac{(6.6262 \times 10^{-34} \, J\,sec)(3 \times 10^{8} \, m/sec)}{540 \times 10^{-9} \, m}$$

$$= \frac{(6.6262)(3)}{540} \times 10^{-34+8+9} \, J$$

$$= 0.0368 \times 10^{-17} \, J$$

$$= 0.368 \times 10^{-18} \, J \quad PER \quad PHOTON$$

ENERGY OF ONE PHOTON $= 0.368 \times 10^{-18} \, J$ $$1 \, J/sec = 1 \, WATT$$

$$\left(1 \, \frac{J}{sec}\right)\left(\frac{PHOTON}{0.368 \times 10^{-18} \, J}\right) = 2.72 \times 10^{18} \, \frac{PHOTONS}{sec}$$

FIG. 9

For photons of wavelength $540 \times 10^{-9}$ m each watt contains $2.72 \times 10^{18}$ photons/sec In whole blood the concentration of HgB is $5.421 \times 10^{18}$ HgB's/ml The volume under consideration for this calculation is a thin disc 10 cm in diameter and 0.013 cm thick which is approximately equal to $1 cm^3$.

At a depth of 0.013 cm and for incident photons of wavelength $540 \times 10^{-9}$ m 84% of the photons are absorbed.

We now make one assumption that there is a one to one quantum relationship between each photon absorbed and photolysis.

FIG. 10

We are interested in a rate reaction such that Watts must relate to flow.

Thus $J/sec \longleftrightarrow ml/sec$

FIG. 11

Consider a flow of $1 ml/sec$ $(5.421 \times 10^{18} \text{ HgB's}/ml)(1 ml/sec) = 5.421 \times 10^{18} \text{ HgB's}/sec$ AND WE WANT TO KNOW HOW MANY Watts ARE NEEDED TO REACT THIS MANY HgB's For $540 \times 10^{-9} m$ wavelength photons we write $(N \frac{J}{sec})(\frac{photon}{0.368 \times 10^{-18} J})(0.84)$ where 0.84 represents the percentage of photons absorbed at a depth of 0.013 cm and $(N \frac{J}{sec})(\frac{photon}{0.368 \times 10^{-18} J})(0.84) = 5.421 \times 10^{18} \text{ HgB's}/sec$ $(N \frac{J}{sec})(2.72 \times 10^{18} \frac{photon}{J})(0.84) = 5.421 \times 10^{18} \text{ HgB's}/sec$ $(N \frac{J}{sec})(2.72 \times 10^{18} \frac{photon}{J}) = 6.454 \times 10^{18} \text{ HgB's}/sec$ $$N \frac{J}{sec} = \frac{6.454 \times 10^{18} \frac{HgB's}{sec}}{2.72 \times 10^{18} \frac{PHOTON}{J}}$$

$$N \frac{J}{sec} = 2.37 \left(\frac{HgB}{PHOTON}\right)\left(\frac{J}{sec}\right) \quad \text{FIG. 12}$$

THEREFORE THE NUMBER OF WATTS NEEDED FOR $1 \frac{HgB}{PHOTON}$ IS 2.37 BASED ON A FLOW RATE OF $1 \frac{ml}{sec}$ HOWEVER THERE ARE FOUR BINDING SITES IN EACH HgB MOLECULE AND AT THIS POINT WE HAVE ASSUMED ONE PHOTON PER BINDING SITE

THUS FROM ABOVE WE WRITE $$N \frac{J}{sec} = 2.37 \left(\frac{HgB}{PHOTON}\right)\left(\frac{4\ BINDING\ SITES}{HgB}\right)\left(\frac{1\ PHOTON}{BINDING\ SITE}\right)\left(\frac{J}{sec}\right)$$

AND $N = 9.48$

THEREFORE 9.48 WATTS ARE NEEDED TO REACT ALL FOUR BINDING SITES OF ALL HgB MOLECULES FOR PHOTONS OF WAVELENGTH $540 \times 10^{-9}$ m AT A FLOW RATE OF $1 \frac{ml}{sec}$

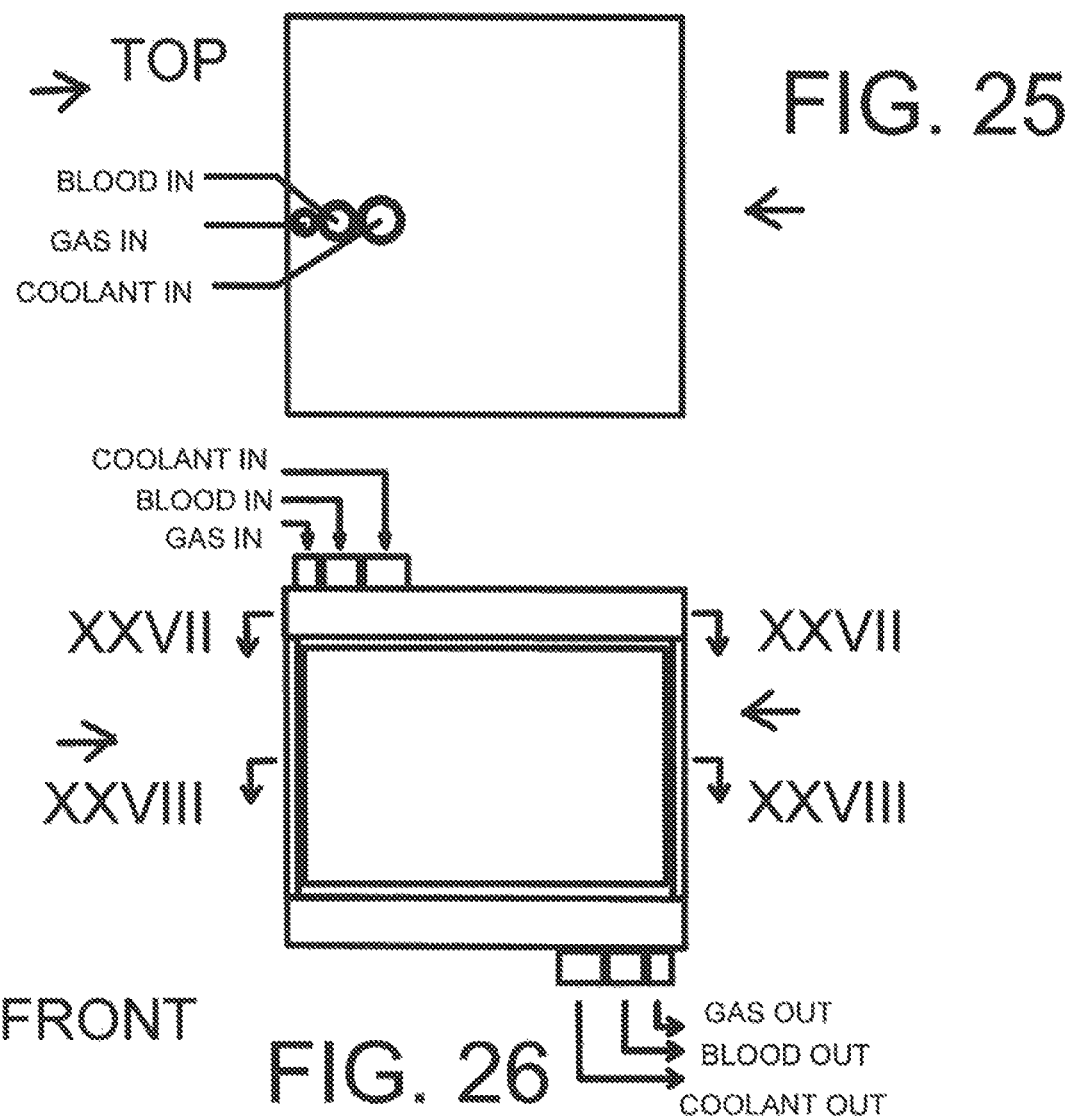

FIG. 31
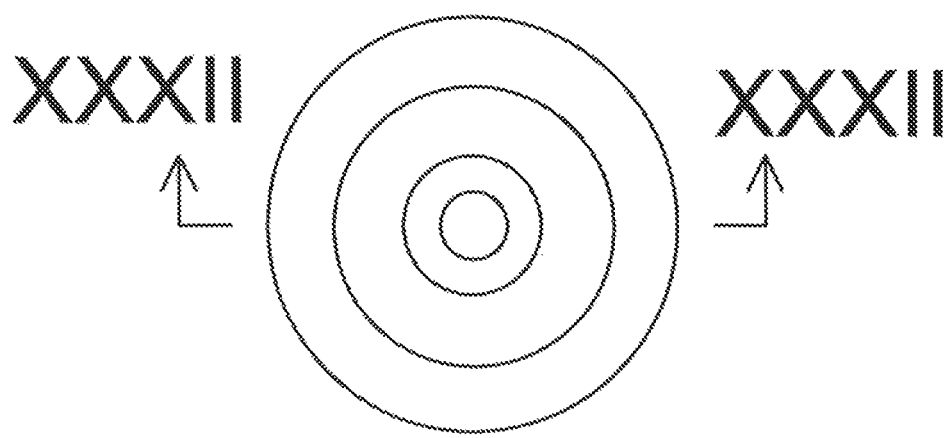
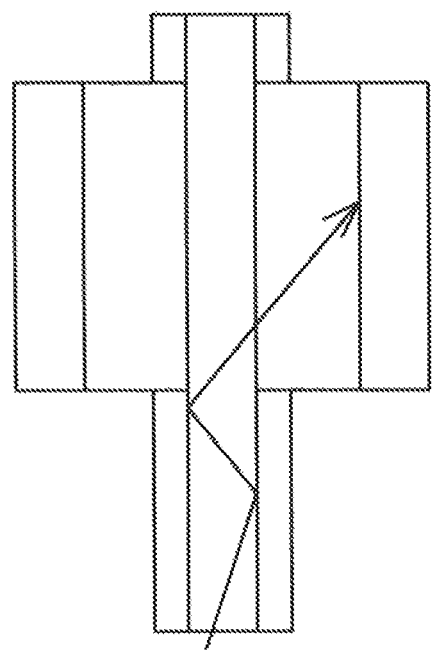
FIG. 32

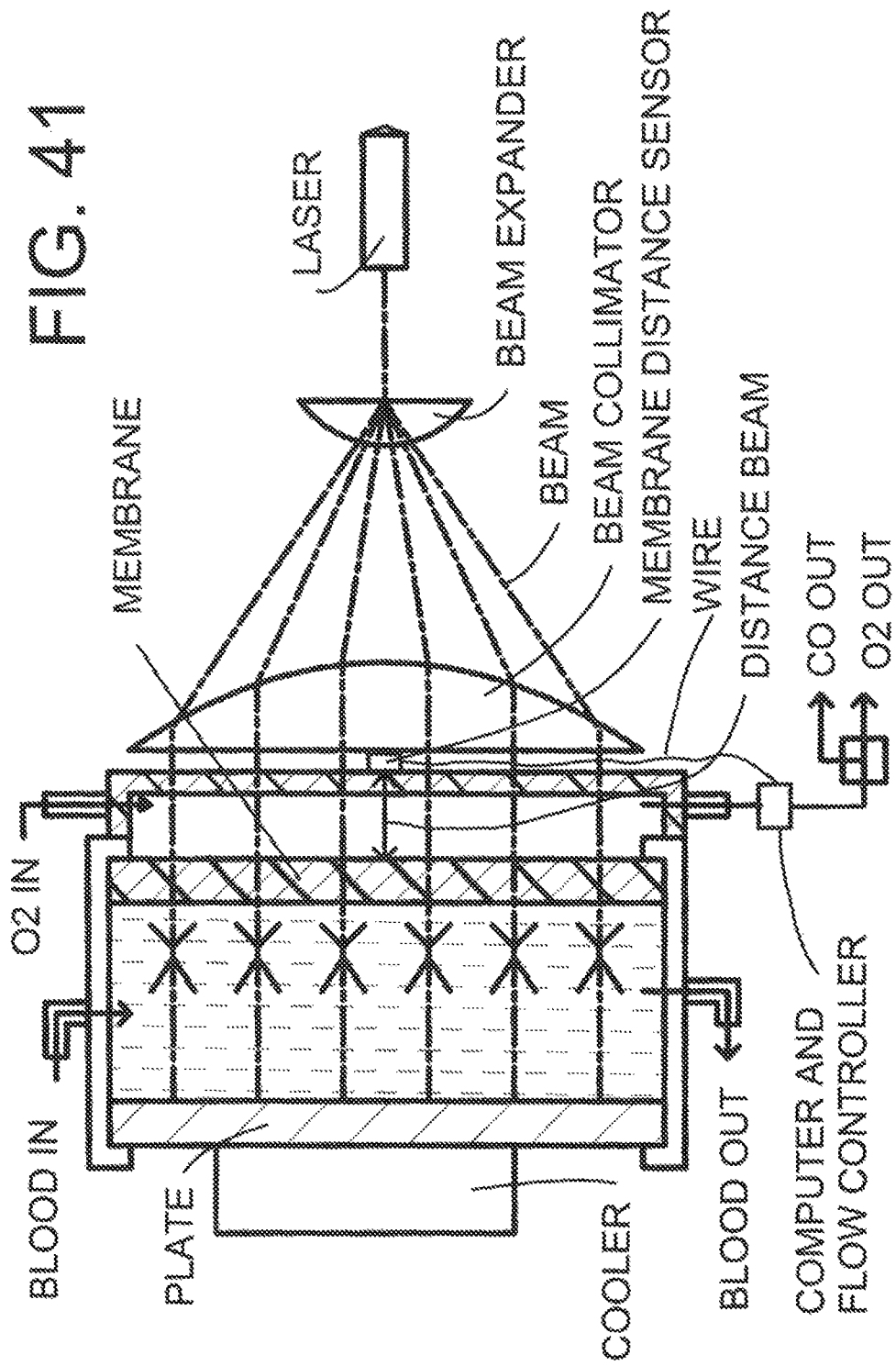

EXTRACORPOREAL PHOTODYNAMIC BLOOD ILLUMINATION (IRRADIATION) FOR THE TREATMENT OF CARBON MONOXIDE POISONING

CROSS-REFERENCE TO RELATED APPLICATIONS

This application claims the benefit under 35 U.S.C. § 119(e) of U.S. Provisional Application No. 61/442,211 filed Feb. 12, 2011, which is hereby incorporated by reference.

STATEMENT REGARDING FEDERALLY SPONSORED RESEARCH OR DEVELOPMENT

This invention has been created without the sponsorship or funding of any federally sponsored research or development program.

FIELD OF THE INVENTION

This invention involves a system for treating carbon monoxide poisoning.

BACKGROUND OF THE INVENTION

Carbon monoxide (CO) poisoning is a well-known phenomenon, and for the most part, its pathophysiology is well-understood. Each year in the United States there are close to 500 deaths, over 15,000 emergency room visits, and approximately 4,000 hospitalizations due to CO poisoning. A review of pertinent background information on the subject can be found at the following Internet links. http://www.cdc.gov/co/faqs.htm, and http://en.wikipedia.org/wiki/Carbon_monoxide_poisoning Current Treatment: At present, the treatment of CO poisoning can be thought of as having three main components: first aid, standard oxygen therapy, and hyperbaric oxygen. First aid consists of immediately removing the victim from the source of CO exposure. Standard oxygen therapy consists of administering 100% oxygen through a tight-fitting non-rebreather mask. This technique results in the administration of high concentrations of oxygen at a level of between 60-90% $O_2$. However, for patients with severe chronic obstructive pulmonary disease (COPD) such high levels of oxygen can actually inhibit their respiratory drive and thus lead to decreased ventilation. Hyperbaric oxygen (HBO) requires the use of a hyperbaric chamber which is found in very select locations and is not always readily available. However, a review published in 2005 on the use of HBO concluded: "There is conflicting evidence regarding the efficacy of HBO treatment for patients with CO poisoning. Methodological shortcomings are evident in all published trials, with empiric evidence of bias in some, particularly those that suggest a benefit of HBO. Bayesian analysis further illustrates the uncertainty about a meaningful clinical benefit. Consequently, firm guidelines regarding the use of HBO for patients with CO poisoning cannot be established. Further research is needed to better define the role of HBO, if any, in the treatment of CO poisoning."

Scientific Background: Following exposure, CO binds to hemoglobin to form carboxyhemoglobin. The affinity between CO and hemoglobin is approximately 230 times stronger than the affinity between oxygen and hemoglobin. Therefore, CO binds to hemoglobin in a much greater likelihood than oxygen. Carbon monoxide also binds to the hemeprotein known as myoglobin. Carbon monoxide also has a high affinity for myoglobin at about 60 times greater than that of oxygen. It should also be noted that a delayed return of symptoms of CO poisoning have been reported and is associated with a recurrence of increased carboxyhemoglobin levels following an initial reduction in the level of carboxyhemoglobin. This effect may be due to a late release of CO from myoglobin, which then subsequently binds to hemoglobin.

Although previously not associated with carbon monoxide poisoning, the basic principle of extracorporial therapy involves the circulation of blood outside of the body. Extracorporial treatment is well-established in the practice of medicine, and the most well-known example is hemodialysis. Another common example is cardiac bypass surgery during which an external pump is used instead of the heart which allows surgeons to operate on a non-beating heart. Two less well-known examples are plasmapharesis and peripheral blood stem-cell harvest.

The application that may appear most pertinent in the setting of CO poisoning is the extracorporeal membrane oxygenator (ECMO). These devices have been shown to play an important role in the clinical management of neonatal infants whose lungs are not developed enough to provide the physiologic function of oxygen absorption and carbon dioxide excretion. An example of such a device and a brief description of its principles of operation can be found at the following Internet link. http://www.ame.hia.rwth-aachen.de/index.php?id=267&type=98&L=1&L=1

It should be noted that the administration of 100% oxygen through a tight-fitting non-rebreather mask reduces the elimination half-life of carboxyhemoglobin to an average of 60 minutes, while HBO at a pressure of between 2.4 and 3 atmospheres reduces the elimination half-life of carboxyhemoglobin to an average of 20 minutes. Based on a five half-life carboxyhemoglobin elimination end-point, this would on average require five hours of 100% oxygen administration or 100 minutes of HBO at pressures noted above.

All of the existing treatments for carbon monoxide poisoning have some drawbacks. These and other difficulties experienced with the prior art devices have been obviated in a novel manner by the present invention.

It is, therefore, an outstanding object of some embodiments of the present invention to provide a system for the treatment of carbon monoxide poisoning in an efficient and effective manner.

Another object of some embodiments of the present invention is to provide a system for the treatment of carbon monoxide poisoning in a cost effective manner.

With these and other objects in view, as will be apparent to those skilled in the art, the invention resides in the combination of parts set forth in the specification and covered by the claims appended hereto, it being understood that changes in the precise embodiment of the invention herein disclosed may be made within the scope of what is claimed without departing from the spirit of the invention.

BRIEF SUMMARY OF THE INVENTION

An extracorporial treatment of carbon monoxide poisoning of a body by removal of a portion of the blood from the body, placing the portion in an exposure cell, exposing the portion in the cell to light of wave length and intensity that causes dissociation of carbon monoxide from hemoglobin, and returning the portion to the body. The intensity and wave length of the light is sufficient to dissociate a therapeutically-effective amount of carbon monoxide from the hemoglobin in the blood. The blood is circulated from and to the body through a concentric double lumen cannula. The wave lengths of the light are 540 and/or 570 nanometers. The cell exposes the blood to at least 9.5 Joules of dissociative light per milliliter of blood, and at least 9.5 Watts of dissociative light per milliliter of blood per second. Oxygen is provided to the system, and the dissociated carbon monoxide is removed from the system.

BRIEF DESCRIPTION OF THE DRAWINGS

The character of the invention, however, may best be understood by reference to one of its structural forms, as illustrated by the accompanying drawings, in which:

FIG. 2 through 12 shows the calculations used to determine the intensity of the desired dissociative light and of the desired wattage of the laser.

FIG. 25 shows a diagrammatic representation of an exposure cell embodying the principles of the present invention, presenting the top view of a exposure cell including four adjacent exposure zones as shown in FIG. 19, FIG. 26 shows a diagrammatic representation of an exposure cell embodying the principles of the present invention, presenting the front elevation view of a exposure cell including four adjacent exposure zones as shown in FIG. 19, FIG. 31 shows a diagrammatic representation of an exposure cell embodying the principles of the present invention, presenting a top view of a internal laser light source that provides laser light to the inward facing window of a surrounding ring of a cylindrical exposure zone, FIG. 32 shows a diagrammatic representation of an exposure cell embodying the principles of the present invention, presenting a sectional front elevation view along line XXX-XXX of FIG. 31.

FIG. 41 shows a diagrammatic representation of an exposure cell embodying some of the principles of the present invention; presenting the basic design, shown in FIG. 13, for an exposure cell that employs a gas-permeable light window. FIG. 41 includes a system for minimizing the distension of the membrane that forms the gas-permeable light window."

DETAILED DESCRIPTION OF THE INVENTION

Figure 1:
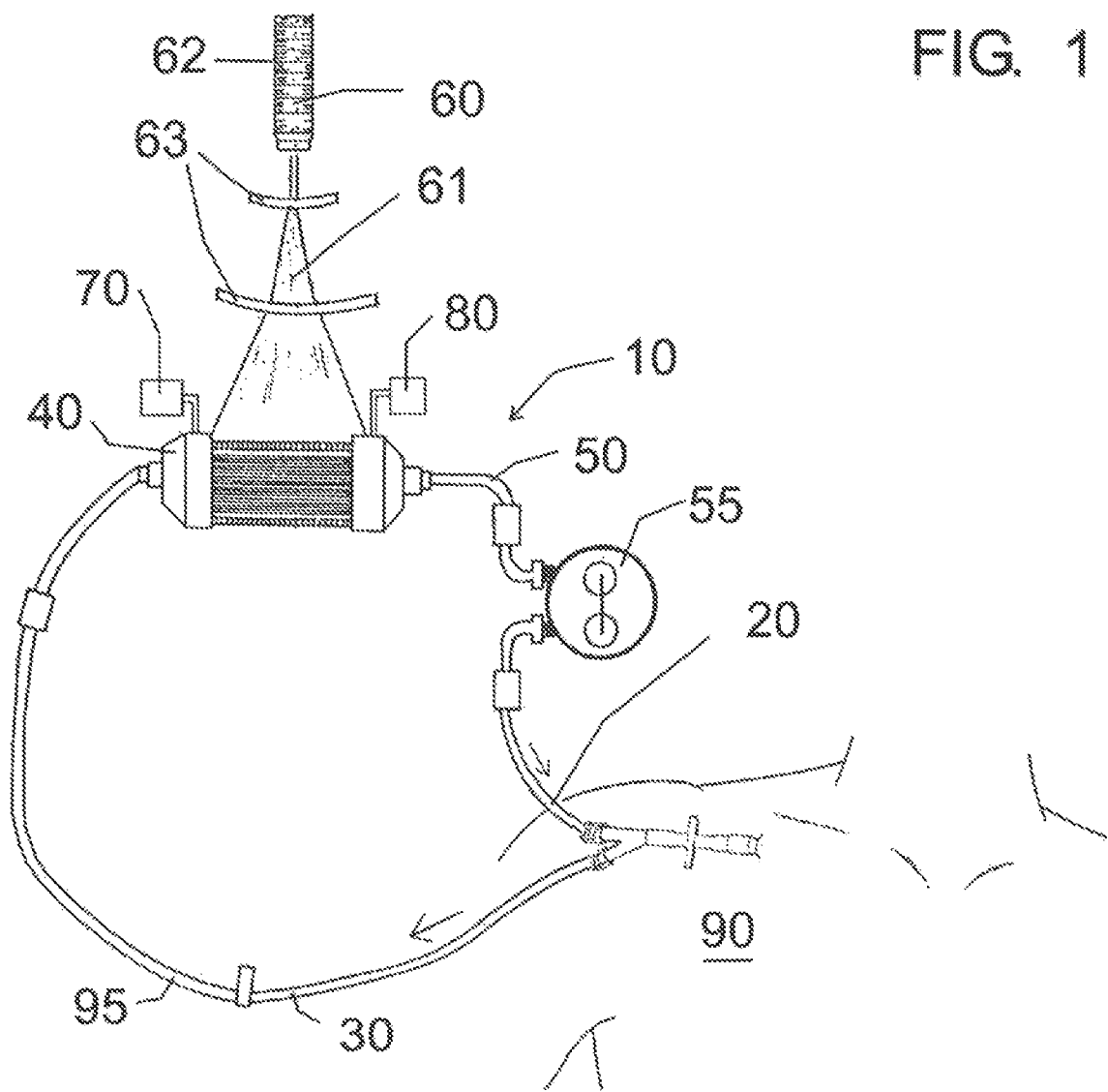
FIG. 1 shows a schematic diagram of a system for treating carbon monoxide poisoning and representing one embodiment of the present invention.

Referring first to FIG. 1 in which the general principles of the present invention are shown, the carbon monoxide treatment system is designated by the numeral 10. The human body is designated by numeral 90. The cannula 20 is inserted into the human 90. The cannula 20 includes a outgoing leg 30 that takes blood 95 out of the body 90, and an incoming leg 50 that puts blood 95 back into the body 90. A cell 40 is positioned between the outboard ends of the outgoing 30 and incoming leg 50 and the blood 95 is circulated through the cell 40. A blood pump 55 in the incoming leg 50 causes the circulation of the blood 95 through the cannula 20.

The cell 40 visually presents the circulating blood 95 to the beam 61 of a laser system 60, that includes the laser 62 itself, and a beam control system 63. An oxygen injector 70 feeds oxygen into the cell 40. A carbon monoxide extractor 80 removes carbon monoxide from the cell 40.

Photochemical research dating back to the 1970's has shown that visible light, particularly in the green portion of the spectrum at the wavelength of 540 nanometers, causes the photodissociation of CO from carboxyhemoglobin. It is upon this principle that this novel approach to the treatment of CO poisoning is based.

When the concept of this new approach in the treatment of CO poisoning was first envisioned, there was a significant technological barrier. An initial calculation was made regarding the amount of visible light that would be required at the 540 nanometer wavelength in order to provide an advantage over standard oxygen therapy and with the approximate equivalence of HBO in the treatment of CO poisoning. Expressed in terms of wattage, and assuming 100% efficiency at a blood flow rate of one milliliter per second, 9.5 Watts of visible light at 540 nanometers is necessary. However, xenon arc lamps and tunable dye lasers were between one and three orders of magnitude below this requirement. Recently, a high power laser system at 540 nanometers with beam coupling by second harmonic generation has been described capable of generating a single beam with an average power of 124 Watts. T. Riesbeck, H. J. Eichler, A High Power Laser System at 540 nm with Beam Coupling by Second Harmonic Generation, Optics Communications 275 (2007) 429-432.

Description and Principles of Apparatus: Based on that which is described above, it becomes a straightforward concept to apply the robust fluence of the visible light generated by the high power laser system at 540 nanometers to an apparatus that is analogous to an ECMO-like device while simultaneously providing standard oxygen therapy. For the discussion which follows, the yet-to-be-named apparatus shall simply be referred to as an "ECMO-like device". It is important to recognize that the antidote to CO poisoning is oxygen. For maximum effectiveness, oxygen would be introduced to the patient by both the tight-fitting non-rebreather mask and by the ECMO-like device in which the CO is photodissociated from the carboxyhemoglogin to subsequently form oxyhemoglobin. This underlying principle can essentially be understood as "photodialysis" and is supported by technology that currently exists and which can be applied, modified, and improved upon.

Optimal Design Issues: There are multiple aspects that must be considered in order to optimize the efficacy of the apparatus as a whole. These relate to the configuration and propagation of the beam produced by the laser, the blood-light contact surface area, the semipermeable membranes within the ECMO-like device, the rate of extraporporeal circulation, and the degree of invasiveness of the procedure itself.

Invasiveness: The invasiveness can easily be kept to a minimum by using a double-lumen central-line catheter. Central-lines are commonly placed in patients on a daily basis throughout the country. There are several approaches that include the jugular, subclavian, and femoral veins. Using the femoral vein is often considered as the safest and easiest. The blood is best removed from the proximal port of the double-lumen catheter and returned to the patient by way of the distal port of the catheter. This reduces the likelihood of mixing successfully treated blood with untreated blood.

Extracorporeal Circulation Rate: A low priming volume is optimal in order to minimize the amount of blood that is outside of the body and not inside the ECMO-like device. However, the most important considerations relate to the volume of blood and its rate of flow inside the ECMO-like device. Determining the optimal volume and flow rate of blood inside the ECMO-like device will be a matter of precise engineering since it is within the ECMO-like device that the photodissociation occurs. There are other additional factors pertinent to this aspect which are described below. Additionally, one or more heat exchangers should be incorporated into extracorporeal circuit in order to maintain the warmth of the blood and prevent a lowering of core body temperature.

Semipermeable Membranes: Any semipermeable membrane that is used must be of a generally small diameter or thickness to facilitate the displacement and release of CO following its photodissociation from carboxyhemoglobin, its replacement with oxygen, and the subsequent removal of the CO. In addition, all semipermeable membranes in use must be completely transparent to visible light at the 540 nanometer wavelength.

Blood-light Contact Surface Area: As noted above, the photochemical reaction resulting in the photodissociation of CO from carboxyhemoglobin is highly optimized at the 540 nanometer wavelength. With the understanding that attenuation of light occurs through the processes of absorption and scatter, it would be expected that the light from the laser would be significantly attenuated in a thin layer of blood and not penetrate that deeply before becoming almost completely absorbed. Thus the photochemical reaction resulting in the photodissociation of CO is essentially a "surface phenomena". This supports the fact that the blood-light contact surface area be made as large as possible in order to optimize the absorption of the laser light as it will mostly occur in a "thin sheet" of blood.

Propagation and Configuration of Laser Light: Based on the above, there are several approaches that can be taken to propagate and configure the light from the laser both in terms of the blood-light contact surface area and the semipermeable membranes through which the blood flows. One possible approach could involve designing the semipermeable membranes as a thin layer of two sheets between which the blood flows. In this situation, the light from the laser would need to be passed through one or more beam expanders to create a large two-dimensional cross-section that matches the surface area of the semipermeable membranes. As an additional improvement to using a single expanded beam, a beam splitter can be used to first generate two beams. Then with the use of mirrors and two sets of beam expanders, it should be possible to illuminate the semipermeable membranes from both sides. This capability would be expected to allow for a greater separation between the two semipermeable membrane sheets which in turn would impact the volume of blood in the ECMO-like device and its extracorporeal rate of flow. Another approach could involve propagating the light from the laser directly into the ECMO-like device using fiber-optic technology. Then by using a series of branching fiber-optic pipes of decreased diameter, the laser light could be made to illuminate an array of semipermeable membranes configured as small diameter tubes inside of which the blood flows. The fiber-optic pipes and semipermeable membrane tubes would be engineered in such a way so as to form a three-dimensional structure so that when illuminated, all of the light produced by the laser is utilized. With the use of fiber-optic technology as described, which is essentially an "inside-out" approach, the ECMO-like device would likely be more compact. Additionally, there may be greater flexibility in terms of the volume of blood inside the ECMO-like device and the corresponding extracorporeal flow rate. Using fiber-optics in some capacity would also reduce or eliminate the use of mirrors, beam splitters, and beam expanders.

Medical Benefits of Effective Treatment of CO Poisoning: Simply stated, the greatest benefit of successful treatment of CO poisoning is the prevention of patient death. As noted in the opening paragraph, there are approximately 500 deaths per year from CO poisoning in the United States. Unfortunately, in the majority of cases of severe CO poisoning, patient death neither can nor will be avoided. However, with the modest assumption that 20% of the deaths can be prevented with prompt and effective treatment using a readily available intervention such as the ECMO-like device as described, one hundred lives might be saved. This corresponds to saving two lives each week on average.

While a reduction in mortality is perhaps the most obvious and immediate benefit of prompt intervention using the ECMO-like device, an equally valuable benefit lies with the prevention of medical complications from severe CO poisoning in those who survive. It is well-described in the literature that CO poisoning often results in significant toxicity to the central nervous system (CNS). Most of the damage from CO poisoning in the CNS is believed to occur in the white matter. Moreover, the effects of significant CO poisoning in the CNS are often irreversible and result in neurologic disability. The long-lasting CNS complications from CO poisoning can leave individuals with permanent neurological deficits that require long-term rehabilitation. Given the fact that there are over 4000 hospitalization each year in the United States due to CO poisoning, the additional cost associated with the life-long care of those affected with neurologic disability from CO poisoning can easily reach into the tens of millions of dollars. Thus in addition to its life-saving benefit in the setting of severe CO poisoning, the ECMO-like device would be expected to make a profound impact in reducing, and in some cases eliminating CNS complications and thereby prevent serious long-term neurological deficits in survivors.

Although not as dramatic as the CNS complications, CO poisoning can also result in cardiac toxicity. Once again, and analogous to what is described in the above paragraph, the ECMO-like device would be expected to favorably reduce the likelihood of permanent heart damage.

Theoretical Considerations: In considering aspects by which the ECMO-like device might be optimally applied, a few circumstances warrant consideration. In the hospital setting, one might envision using several ECMO-like devices while simultaneously administering HBO. In this situation, the patient would be required to be inside a hyperbaric chamber with two or more double-lumen catheters placed as central-lines in either the jugular, subclavian, or femoral veins and with each one connected to an ECMO-like device. While this seemingly represents "maximum effective therapy", the practicality of this approach is rather questionable and its true advantage is likely in doubt. In the prehospital setting, one might envision a more useful application. Emergency medical service (EMS) personnel are currently trained in various life-saving techniques which include cardiac defibrillation and starting peripheral intravenous lines. With technological advances, the ECMO-like device will likely become more miniaturized, both in terms of the laser light source and all of the associated engineering. Once the diagnosis of CO poisoning is made, paramedicics would be able to initiate the photodissociation by using a suitable double-lumen catheter along with standard oxygen therapy. Actions taken in this regard by EMS personnel well in advance of their arrival to the hospital are not only logistically possible, but would also provide a genuine time advantage in terms of maximizing the available and effective treatment of CO poisoning in the prehospital setting.

In the preferred embodiment of the invention, the cell would be provided with a system to inject oxygen into the cell and treated blood. This would encourage the hemoglobin, from which the carbon monoxide has been dissociated, to take up oxygen. That would discourage reassociation of dissociated carbon monoxide back into the hemoglobin.

Also, in the preferred embodiment of this invention, the cell in which the carbon monoxide would be dissociated from the blood is provided with a venting system that would capture and isolate the dissociated carbon monoxide from the cell. This would reduce the back-pressure of the carbon monoxide in the cell from slowing the dissociation. Furthermore, preferred system would prevent the venting of the carbon monoxide into the environment of the equipment. This same principle should be applied to other, existing carbon monoxide treatment systems. The conventional high pressure oxygen mask, used in an emergency room, vents the dissociated carbon monoxide into the room. This exposes the other emergency room people, including the patients and staff, to the carbon monoxide. The cumulative and long-term aspects of carbon monoxide poisoning, and the special vulnerability of certain types of patients, suggest that this unmanaged venting to the carbon monoxide to the emergency room may not be desirable.

Utility Patent Application for Reaction Chamber

This patent application is in direct support of U.S. Pat. No. 8,858,880, which was issued on 14 Oct. 2014. U.S. Pat. No. 8,858,880 is titled "Extracorporeal Photodynamic Blood Illumination (Irradiation) for the Treatment of Carbon Monoxide Poisoning". Included within the patent is a description of the proposed reaction chamber in which the photodissociation of carbon monoxide from whole blood is to take place. Briefly, the reaction chamber described in U.S. Pat. No. 8,858,880 is based on a single 10 Watt laser from which the beam is split into two 5 Watt sub-beams, and each sub-beam is used to illuminate opposite sides of two parallel sheets of semi-permeable membranes. Each of the two parallel sheets is configured in a square geometry and measures 10 cm.times.10 cm. The separation between the two sheets is 1 mm, and whole blood is designed to flow between the two parallel sheets of semi-permeable membranes. However, existing technology does not support this design.

The two major hurdles that must be overcome in order to construct a practical and usable reaction chambers include the laser light source along with the size and configuration of the semi-permeable membranes. The light source is likely the easier issue to resolve and is first described below.

While a single 10 Watt laser can be constructed, its length, size, and cost become problematic. Fortunately, it is the total power of 10 Watts which is the most important aspect. Therefore, as long as the total power equals 10 Watts, it is less of a consequence if this total power is obtained by using two 5 Watt lasers, three 3.3 Watt lasers, four 2.5 Watt lasers, five 2 Watt lasers, or even ten 1 Watt lasers. As the power of a laser decreases, so does its length, size, and cost. Currently available technology suggests the use of lasers with a power of between 1 and 3 Watts. As described below for the planar designs, the primary beam of each laser is first passed through a beam expander which expands the beam diameter to the size which is required to match the dimensions of the semi-permeable membrane. The light of the expanded beam is directed so that it is incident to the semi-permeable membrane in a perpendicular fashion, which is also known as orthogonal. In all of the designs described below, the laser light that is introduced into the reaction chamber is at the photodissociation wavelength(s).

The more challenging technology is that of the semi-permeable membranes. Two important articles that support the current designs in this patent application have been published in the journal "Biomaterials" and serve as key references. The first article is titled, "A nonthrombogenic gas-permeable membrane composed of a phospholipid polymer skin film adhered to a polyethylene porous membrane" by Y. Iwasaki, et. al. The second article is titled, "Ultra-thin, gas permeable free-standing and composite membranes for microfluidic lung assist devices" by R. Sreenivasan, et.al.

FIG. 6 in the Iwasaki paper illustrates the fundamental concept of what is required for the performance of the PMD/PE porous membrane. Details are described on page 3426. In summary, for the surface of the semi-permeable membrane that is in contact with the blood, the PMD film reduces both plasma protein adsorption as well as the adhesion of the cellular components of the blood. Water does not penetrate into the layer constituting the PE porous membrane, and there is also no leakage of plasma. However, oxygen gas is able to penetrate freely through the PE porous membrane, through the PMD film, and directly into the blood.

On page 3884 in the paper by Sreenivasan. the following is included. "For the purposes of this article we define an ultra-thin large surface area membrane to be a membrane with thickness less than 10 .mu.m and spanning not less than 50 cm2." It is further stated by Sreenivasan that "Ultra-thin permeable membranes need to be mechanically robust enough to cover many square centimeters on a microfluidic device with the free-standing (unsupported) parts of the membrane spanning microfluidic channels ranging from the .mu.m to mm range". In the paper by Iwasaki, the total thickness of the composite membrane is 33 .mu.m. while in the paper by Sreenivasan, the membrane thickness is much smaller at only 5 .mu.m. However, the size of the membranes that were created is similar in both papers. In the paper by Iwasaki, the membrane is oval in shape and measured 2.5 cm.times.5 cm or approximately 125 cm2. In the paper by Sreenivasan, the membrane is circular in shape and had an initial diameter of 5.08 cm, or radius of 2.54 cm. This corresponds to an area of 20.27 cm2. However, for testing purposes, the membrane is supported by a handling template, and the size used for subsequent analysis is 2.54 cm in diameter. This corresponds to a radius of 1.27 cm, and results in an area of 5 cm2. From the above description, one can conclude that semi-permeable membranes currently available for use on a practical basis would typically have a length ranging between 3 cm to 6 cm which would correspond to areas ranging between 10 cm2 and 30 cm2. However, as noted by Sreenivasan, areas on the order of 50 cm2 are expected to be achievable. As a reference for what is described below, and assuming a square geometry rather than an oval or circular geometry, a 3 cm.times.3 cm semi-permeable membrane has an area of 9 cm2, a 4 cm.times.4 cm semi-permeable membrane has an area of 16 cm2, a 5 cm.times.5 cm semi-permeable membrane has an area of 25 cm2, and a 6 cm.times.6 cm semi-permeable membrane has an area of 36 cm2. It should be noted that a 7 cm.times.7 cm semi-permeable membrane has an area of 49 cm2, which is consistent with the size described by Sreenivasan.

As described at the beginning of this application, a 10 cm.times.10 cm semi-permeable membrane. which has an area of 100 cm2, is essentially twice the size of what is economically practical at the present time. Although areas of semi-permeable membranes will almost certainly increase in the future, the design of the reaction chamber for the treatment of carbon monoxide poisoning must take these current limitations into account. In this regard, the following new designs are now described.

The two different designs are based on either a planar shape or a cylindrical shape and with either an external or internal light source. The description begins with the planar shape.

Planar Design With External Light Source

The basic principle in the planar design of the reaction chamber can simply be described as "economy of size". This is accomplished by scaling down the 10 cm.times.10 cm semi-permeable membrane to a smaller dimension, utilizing several lower-power lasers, and illuminating the semi-membrane from only one side. As noted above, semi-permeable membranes must be mechanically robust in spite of being extremely thin. A semi-permeable membrane with a thickness on the order of 20 .mu.m will lose structural rigidity as its total area increases. As an analogy, we are all familiar that a large sheet of paper is more prone to bending and folding than a piece of paper which is much smaller.

The reaction chamber can be designed according to existing technology and therefore consists of either two, three, four, five, or six exposure cells, although it could be scalable to as few as a single exposure cell or perhaps to as many as ten exposure cells. The reaction chamber in each of the different cases consists of either two identical, three identical, four identical, five identical, or six identical exposure cells. In other words, the size of the exposure cell is the same in each case as described as follows.

The front side of the exposure cell consists of the semi-permeable membrane. The back side of the exposure cell is made of metal and consists of an inner side, which is the blood side, and an outer side. The inner side of the back side of the exposure cell, which is the blood side, consists of a highly-polished metal that is 100% reflective to visible light. The semi-permeable membrane of each exposure cell is supported by a handling template, and there is a gap of 1 mm between the semi-permeable membrane (front side) and the inner side (blood side) of the back side of the exposure cell. Blood flows through the exposure cell inside the 1 mm gap. The total area of the semi-permeable membranes of all exposure cells taken together is equal to approximately 100 cm2. Thus for two exposure cells, the area of each is 50 cm2. For three exposure cells, the area of each is 36 cm2. For four exposure cells, the area of each is 25 cm2. For five exposure cells, the area of each is 20 cm2. For six exposures cells, the area of each is 16 cm2. The total area of the gap through which the blood flows is as follows. For a single exposure cell, the area of the gap is 1 cm2. For two exposure cells, the total area of the gap is 1.4 cm2. For three exposure cells, the total area of the gap is 1.8 cm2. For four exposure cells, the total area of the gap is 2 cm2. For five exposure cells, the total area of the gap is 2.2 cm2. For six exposures cells, the total area of the gap is 2.4 cm2.

In a two exposure cell reaction chamber, two 5 Watt lasers are used. In a three exposure cell reaction chamber, three 3.3 Watt lasers are used. In a four exposure cell reaction chamber, four 2.5 Watt lasers are used. In a five exposure cell reaction chamber, five 2 Watt lasers are used. In a six exposure cell reaction chamber, six 1.67 Watt lasers are used. As noted above, the laser light that is introduced into the reaction chamber is at the photodissociation wavelength(s).

Other than the two exposure cell reaction chamber which is described separately, the reaction chamber that consists of three, four, five, or six exposure cells is constructed in a symmetric fashion, such that the cross-section through the reaction chamber at mid-level forms either a triangle, square, pentagon, or hexagon.

Blood comes from the patient in a single tube and enters the reaction chamber where it is first divided by a manifold. The manifold is constructed to equally divide and direct the blood according to the number of exposure cells. Blood leaving the exposure cells enters another manifold which combines the blood from each of the exposure cells. Blood then leaves the reaction chamber in a single tube and is subsequently returned to the patient.

In addition to the photodissociation of carbon monoxide from hemoglobin, the absorption of laser light by the blood also results in a transfer of energy in the form of heat. As described in U.S. Pat. No. 8,858,880, heat exchangers are employed in order to maintain the temperature of the blood close to that of normal body temperature, which is 37.degree. C. A heat energy transfer analysis has been conducted and the results reveal that the temperature rise of the blood secondary to the laser-induced photodissociation is modest and can be controlled without much difficulty. As noted above, the inner side (blood side) of the back side of the exposure cells consists of a highly-polished metal that is 100% reflective to visible light, while the outer side of the back side of the exposure cells, which is also metal, does not require a highly-polished surface. Behind the outer side of the back side of the exposure cells there is an available space which has a geometry that depends upon whether the reaction chamber consists of two, three, four, five, or six exposure cells. As metal is also an excellent conductor of heat, it is within this space through which a liquid is circulated that is in direct contact with the outer side of the back side of the exposure cells. The temperature of the circulated liquid and its rate of flow are controlled in order to maintain the blood at the desired temperature.

The design of the two exposure cell reaction chamber follows the same principles as described above, but has a somewhat different configuration, while being slightly similar to the reaction chamber described in U.S. Pat. No. 8,858,880. The modified version of the two exposure cell reaction chamber consists of four parallel surfaces. There is a front side (semi-permeable membrane), gap of 1 mm, back side, space, back side, gap of 1 mm, and then another opposite front side (semi-permeable membrane). In essence, the two exposure cell reaction chamber consists of two single exposure cells "back-to-back" with an available space located between the two back sides. Similar to what is described above, it is within this space through which a liquid is circulated that is in direct contact with the back side of the two exposure cells. The width of the space is optimized and the temperature of the circulated liquid and its rate of flow are controlled in order to maintain the desired temperature of the blood, which flows through the 1 mm gap of each exposure cell. For all of the designs described above, the laser light is incident on the semi-permeable membrane, which is the front side of each of the exposure cells. In the case of the two exposure cell reaction chamber, the laser light at the photodissociation wavelength(s) is directed at the two semi-permeable membranes that form the two opposite front sides.

The exposure cells of the reaction chamber are encased in a sealed glass structure that is constructed in a symmetric fashion such that the cross-section at mid-level forms either a rectangle, triangle, square, pentagon, or hexagon, depending upon if there are two, three, four, five, or six exposure cells respectively. The sealed glass structure is designed such that there is a space between the inner side of the glass and the front side of the exposure cell, which is the semi-permeable membrane. Once the laser beam is expanded to the necessary dimension to match the size of the exposure cell, the laser light is incident on the outer side of the glass. The light propagates through the glass, across the open space, and is then incident on the front side of the exposure cells, which is the semi-permeable membrane.

One-hundred percent oxygen is introduced inside the reaction chamber into the space between the inner side of the glass and the front side of the exposure cells, which is the semi-permeable membrane. The oxygen pressure and flow are optimized so as not to impede the flow of blood inside the 1 mm gap. Following the photodissociation, the excess oxygen along with the eliminated carbon monoxide exit the reaction chamber and flow to an external trap where the carbon monoxide is captured, after which the remaining oxygen is vented.

Planar Design With Internal Light Source

The basic principle for the planar design with an internal light source can simply be described as the same geometry of the planar design with the external light source but with the exposure cells "flipped outside in". However, there are several important differences.

As in the previous design, the reaction chamber that consists of three, four, five, or six exposure cells is constructed in a symmetric fashion, such that the cross-section through the reaction chamber at mid-level forms either a triangle, square, pentagon, or hexagon.

The design of the two exposure cell reaction chamber consists of four parallel surfaces with the two semi-permeable membranes facing each other separated with a gap of at least several centimeters.

The exposure cells of the reaction chamber are encased in a sealed outer structure that is constructed in a symmetric fashion such that the cross-section at mid-level forms either a rectangle, triangle, square, pentagon, or hexagon, depending upon if there are two, three, four, five, or six exposure cells respectively. The sealed outer structure is designed such that there is a space between the inner side of the sealed outer structure and the back side of the exposure cells, which is made of metal that does not require a highly-polished surface. It is within the space between the sealed outer structure and the outer side of the back side of the exposure cells through which a liquid is circulated that is in direct contact with the outer side of the back side of the exposure cells. The temperature of the circulated liquid and its rate of flow are controlled in order to maintain the blood at the desired temperature.

Laser light at the photodissociation wavelength(s) is introduced to the geometric center of the reaction chamber, which is likely to be accomplished with fiber-optic technology, and by using the required number of lasers to match the number of exposure cells so that the total power is 10 Watts. The primary beam of each laser is first passed through a beam expander which expands the beam diameter to the size which is required to match the dimensions of the semi-permeable membrane of each exposure cell. The light of the expanded beam is directed so that it is incident to the semi-permeable membrane in a perpendicular fashion.

One-hundred percent oxygen is introduced into the central space inside the reaction chamber. The oxygen pressure and flow are optimized so as not to impede the flow of blood inside the 1 mm gap. Following the photodissociation, the excess oxygen along with the eliminated carbon monoxide exit the reaction chamber and flow to an external trap where the carbon monoxide is captured, after which the remaining oxygen is vented.

Cylindrical Design With Internal Light Source

The basic principle in the cylindrical design of the reaction chamber can simply be described as a circular geometry of the exposure cell. As with the planar design, the total area of the semi-permeable membranes of the exposure cell is equal to approximately 100 cm2. With a height of 2.5 cm and a diameter of 12.74 cm (radius of 6.37 cm), an open cylinder without a closed top and bottom has an area of 100 cm2. Similarly, with a height of 3 cm and a diameter of 10.62 cm (radius of 5.31 cm), an open cylinder without a closed top and bottom has an area of 100 cm2. With a height of 4 cm and a diameter of 7.96 cm (radius of 3.98 cm), an open cylinder without a closed top and bottom has an area of 100 cm2. With a height of 5 cm and a diameter of 6.38 cm (radius of 3.19 cm), an open cylinder without a closed top and bottom has an area of 100 cm2.

The design of the cylindrical exposure cell consists of three concentric cylinders all of which have the same central axis. The inner concentric cylinder is the semi-permeable membrane. The middle concentric cylinder is made of metal and consists of an inner side, which is the blood side, and an outer side. The outer concentric cylinder is of a larger diameter and allows for a space between it and the outer side of the middle concentric cylinder. Details are described below.

The design of the cylindrical exposure cell begins with the inner and middle concentric cylinders and is constructed so that there is a 1 mm gap between the two cylinders. It is within this gap through which the blood flows. Using the four examples from above, for a height of 2.5 cm, the diameters are 12.74 cm and 12.94 cm (radii of 6.37 cm and 6.47 cm). For a height of 3 cm, the diameters are 10.62 cm and 10.82 cm (radii of 5.31 cm and 5.41 cm). For a height of 4 cm, the diameters are 7.96 cm and 8.16 cm (radii of 3.98 cm and 4.08 cm). For a height of 5 cm, the diameters are 6.38 cm and 6.58 cm (radii of 3.19 cm and 3.29 cm). The total area of the gap through which the blood flows is as follows. For a height of 2.5 cm, the total area of the gap is 4 cm2. For a height of 3 cm, the total area of the gap is 3.37 cm2. For a height of 4 cm, the total area of the gap is 2.54 cm2. For a height of 5 cm, the total area of the gap is 2 cm2.

The inner concentric cylinder of the exposure cell consists of the semi-permeable membrane. The middle concentric cylinder is made of metal and consists of an inner side, which is the blood side, and an outer side. The semi-permeable membrane of the exposure cell, which is the inner concentric cylinder, is supported by a handling template, and as noted above, there is a gap of 1 mm between the semi-permeable membrane (inner concentric cylinder) and the inner side (blood side) of the middle concentric cylinder of the exposure cell. The inner side of the middle concentric cylinder of the exposure cell, which is the blood side, consists of a highly-polished metal that is 100% reflective to visible light. As noted above, blood flows through the exposure cell inside the 1 mm gap.

Blood comes from the patient in a single tube and enters the reaction chamber where it is first divided by a funnel-shaped manifold. The manifold directs the blood to the 1 mm gap between the semi-permeable membrane (inner concentric cylinder) and the inner side (blood side) of the middle concentric cylinder of the exposure cell. Blood leaving the exposure cells enters another funnel-shaped manifold which combines the blood from the 1 mm gap between the semi-permeable membrane (inner concentric cylinder) and the inner side (blood side) of the middle concentric cylinder of the exposure cell. Blood then leaves the reaction chamber in a single tube and is subsequently returned to the patient.

As noted above, the design of the cylindrical exposure cell begins with the inner and middle concentric cylinders. The inner and middle concentric cylinders are encased in a sealed structure by the outer concentric cylinder, which is of a larger diameter than the middle concentric cylinder. As described in the planar design, the absorption of laser light by the blood also results in a transfer of energy in the form of heat. As noted above, the inner side of the middle concentric cylinder of the exposure cell, which is the blood side, consists of a highly-polished metal that is 100% reflective to visible light. The outer side of the middle concentric cylinder of the exposure cell is also made of metal that does not require a highly-polished surface. Between the outer side of the middle concentric cylinder and the sealed outer concentric cylinder there is an available space through which a liquid is circulated that is in direct contact with the outer side of the middle concentric cylinder of the exposure cell. The diameter of the outer concentric cylinder, and hence the difference between the diameter of the middle concentric cylinder and the diameter of the outer concentric cylinder is optimized, and the temperature of the circulated liquid and its rate of flow are controlled in order to maintain the desired temperature of the blood, which flows through the 1 mm gap between the inner concentric cylinder and the middle concentric cylinder.

The final component of the cylindrical design is the laser light source and the method of exposing the inner side of the inner concentric cylinder (the semi-permeable membrane). Unlike the planar design, highly-specialized optics is required. As previously noted, a total power of 10 Watts is needed. However, the output of several lower-wattage lasers can be combined so that the total power is equal to 10 Watts. In the cylindrical design of the reaction chamber, 10 Watts of laser light at the photodissociation wavelength(s) is introduced to the geometric center of the three concentric cylinders, which is likely to be accomplished with fiber-optic technology. The laser light is then distributed in an outward radial fashion to expose the semi-permeable membrane over its entire cylindrical length, which will likely be either 4 cm or 5 cm. It should also be noted that with the light dispersed from the geometric center of the inner concentric cylinder, almost all of the available photons will be used to induce the photodissociation of carbon monoxide from the circulated blood.

One-hundred percent oxygen is introduced inside the reaction chamber into the space inside the inner concentric cylinder. The oxygen pressure and flow are optimized so as not to impede the flow of blood inside the 1 mm gap. Following the photodissociation, the excess oxygen along with the eliminated carbon monoxide exit the reaction chamber and flow to an external trap where the carbon monoxide is captured, after which the remaining oxygen is vented.

Cylindrical Design With External Light Source

The basic principle for the cylindrical design with an external light source can simply be described as the same geometry as the cylindrical design with the internal light source, but with the exposure cell "flipped inside out". However, there are several important differences.

The inner concentric cylinder of the exposure cell is made of metal and consists of an inner side, that does not require a highly-polished surface, and an outer side, which is the blood side, that consists of a highly-polished metal that is 100% reflective to visible light. The middle concentric cylinder consists of the semi-permeable membrane, and there is a gap of 1 mm between the semi-permeable membrane (middle concentric cylinder) and the outer side (blood side) of the inner concentric cylinder of the exposure cell. The semi-permeable membrane of the exposure cell, which is the middle concentric cylinder, is supported by a handling template, and blood flows through the exposure cell inside the 1 mm gap.

Inside the inner concentric cylinder there is a space through which a liquid is circulated that is in direct contact with the inner side of the inner concentric cylinder of the exposure cell. The temperature of the circulated liquid and its rate of flow are controlled in order to maintain the desired temperature of the blood, which flows through the 1 mm gap between the inner concentric cylinder and the middle concentric cylinder, which is the semi-permeable membrane.

The inner and middle concentric cylinders are encased by the outer concentric cylinder which is made of glass rather than metal. The outer concentric cylinder has a larger diameter than the middle concentric cylinder which allows for a space between it and the outer side of the middle concentric cylinder, which is the semi-permeable membrane.

The final component of this cylindrical design is the laser light source and the method of exposing the outer side of the middle concentric cylinder (the semi-permeable membrane). Unlike the planar design, highly-specialized optics is required. As previously noted, a total power of 10 Watts is needed. However, the output of several lower-wattage lasers can be combined so that the total power is equal to 10 Watts. In this cylindrical design of the reaction chamber, 10 Watts of laser light at the photodissociation wavelength(s) is initially introduced around the circumference of the outer concentric cylinder, and which is likely to be accomplished with fiber-optic technology. The laser light is then directed in an inward radial fashion to expose the semi-permeable membrane over its entire cylindrical length, which will likely be either 4 cm or 5 cm. The light propagates through the glass, across the open space, and is then incident on the outer side of the middle concentric cylinder of the exposure cell, which is the semi-permeable membrane. It should also be noted that the fiber-optic technology and beam expansion techniques to accomplish the distribution of laser light.

One-hundred percent oxygen is introduced inside the reaction chamber into the space between the middle concentric cylinder (the semi-permeable membrane) and the outer concentric cylinder, which is glass. The oxygen pressure and flow are optimized so as not to impede the flow of blood inside the 1 mm gap. Following the photodissociation, the excess oxygen along with the eliminated carbon monoxide exit the reaction chamber and flow to an external trap where the carbon monoxide is captured, after which the remaining oxygen is vented.

Alternative Exposure Concept

Instead of using a gas-permeable membrane, the poisoned blood could have the disassociated carbon monoxide extracted, by bubbling oxygen through it, exposing the poisoned blood to the laser light, and then harvesting the resulting bubbles of carbon monoxide.

Figure 37:
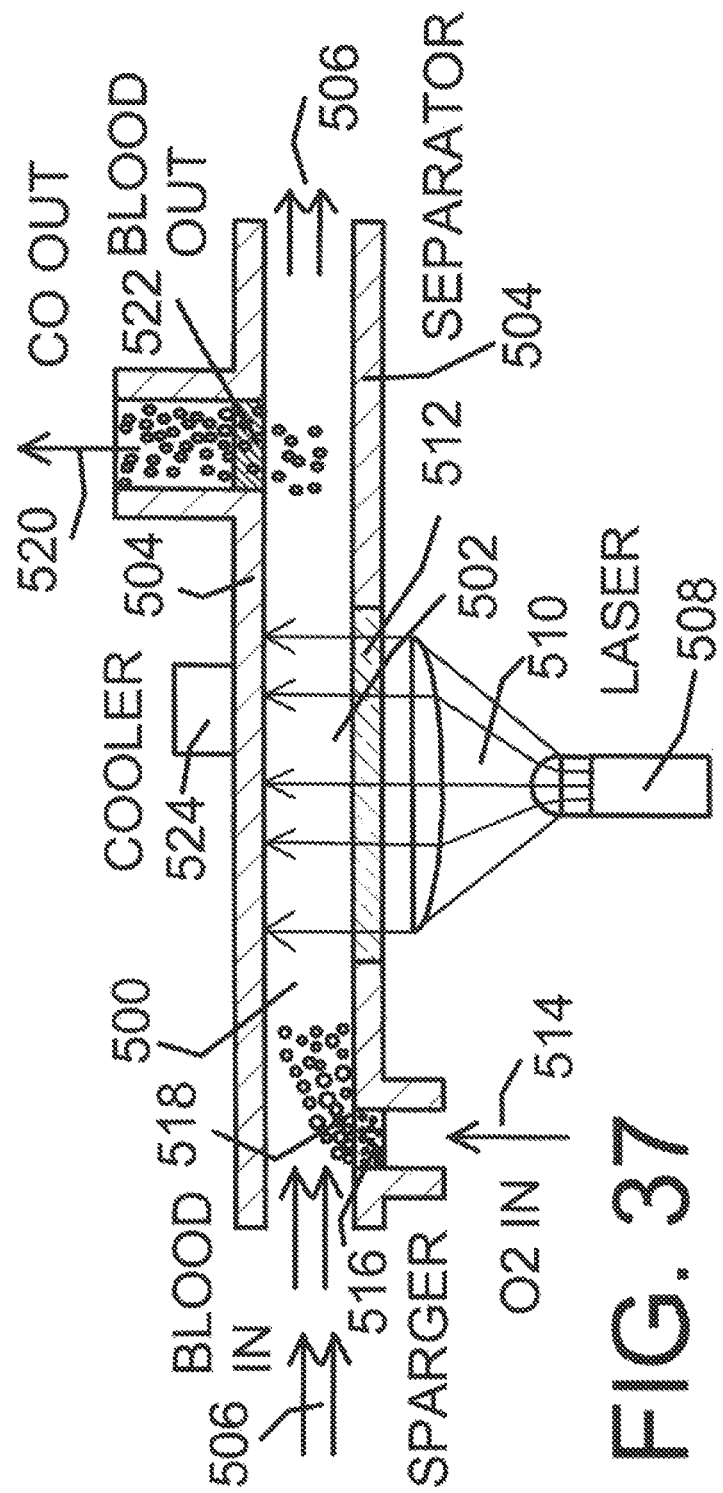
FIG. 37 shows a diagrammatic representation of an alternative exposure cell embodying the principles of the present invention, in which the light window is not gas permeable. Instead of using a gas-permeable membrane, the poisoned blood could have the disassociated carbon monoxide extracted, by bubbling oxygen through it, exposing the poisoned blood to the laser light, and then harvesting the resulting bubbles of carbon monoxide.

The use of a gas permeable membrane to allow the oxygen into the blood and the carbon monoxide out of the blood is a desirable approach, but another approach would use a gas impermeable laser light window, with oxygen bubbled into the blood upstream of the laser exposure zone, and the carbon monoxide bubbled out of the blood downstream of the laser exposure zone. FIG. 37 shows an embodiment of such a concept.

This embodiment of the exposure cell 500 has a laser exposure zone 502, through which a stream of blood 506 passes. The laser exposure zone 502 is defined by a wall 504. The blood stream 506 is extracted from the body of the carbon-monoxide-poisoned person and is returned to the body of the carbon-monoxide-poisoned person, after the blood is treated.

The basic version of this exposure cell, as shown in FIG. 37, has a laser exposure zone 502 with a laser 508 shining appropriate light 510 into the zone 502 through laser transparent, but gas-impermiable window 512, in the wall 504.

Upstream of the exposure cell 500, an oxygen stream 514 is injected into the blood stream 506 through a sparger 516 that breaks the oxygen stream 514 into tiny oxygen bubbles 518 from which the oxygen is quickly desolved into the blood.

Downstream of the exposure cell 500, an carbon monoxide stream 520 is formed when carbon monoxide is released from the blood stream 506 through a separator 522 that separates the carbon monoxide from the blood, for example, by allowing carbon monoxide to pass through a separator plate, while not allowing the blood to pass through the plate.

A cooler 524 cools the wall 504 of the exposure cell 502, and thereby the blood in the cell, to keep the blood at the optimum temperature.

Figure 38:
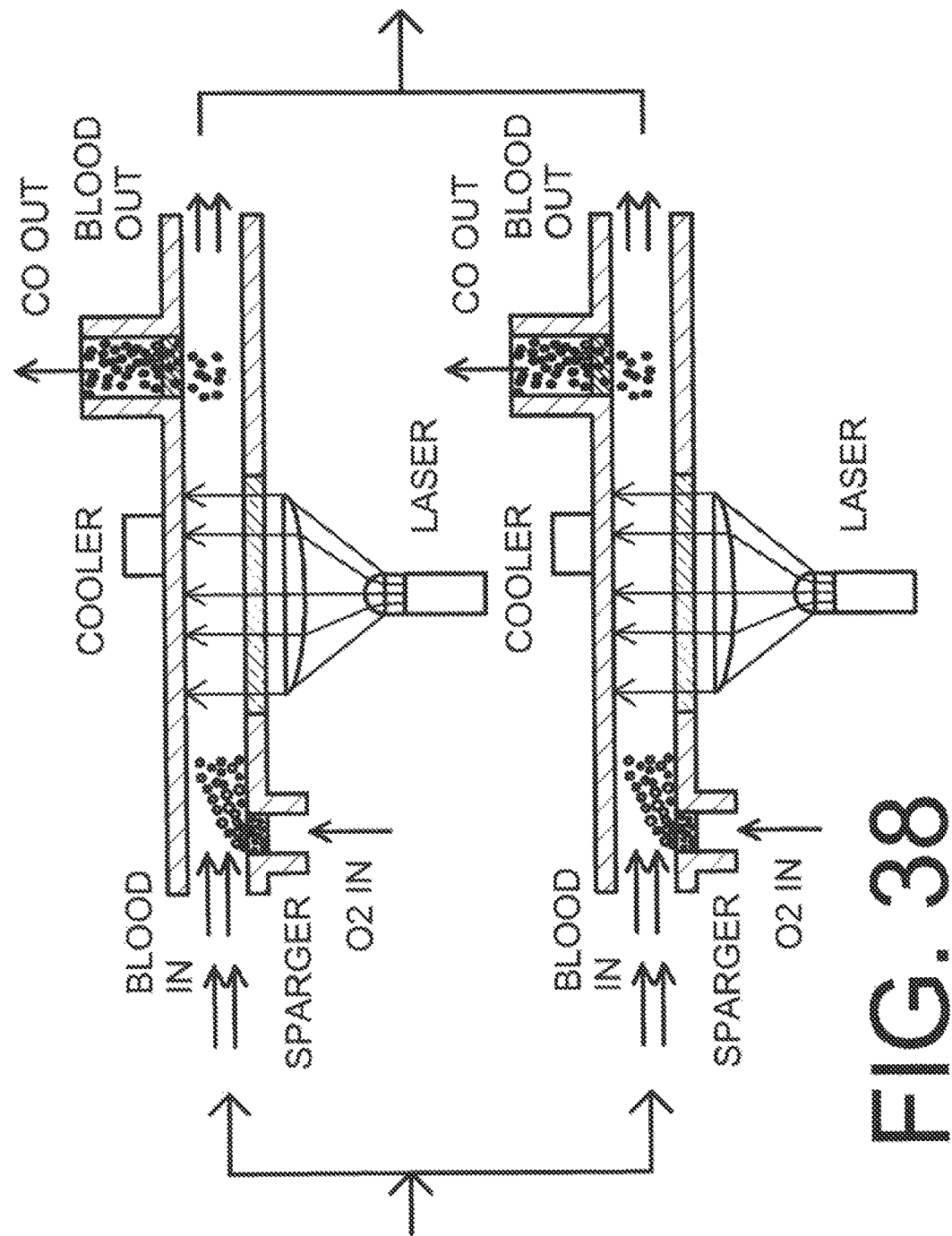
FIG. 38 shows a variation of the concept shown in FIG. 37, in which two (or more) parallel exposure units are arranged so that the blood stream is exposed to a greater amount for laser light per unit time.

FIG. 38 shows a variation of this concept in which two (or more) parallel exposure units are arranged so that the blood stream is exposed to a greater amount for laser light per unit time. This increases the amount of carbon monoxide removed from the blood per unit time.

Figure 39:
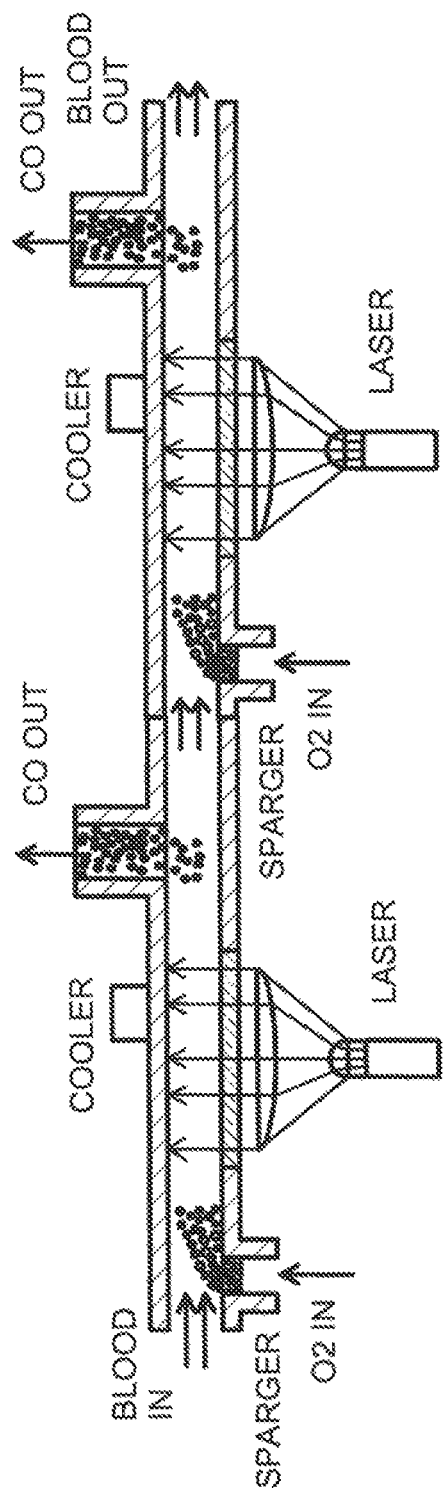
FIG. 39 shows a variation of the concept shown in FIG. 37, in which two (or more) series exposure units are arranged so that the blood stream is exposed to a greater amount for laser light per unit time. This increases the amount of carbon monoxide removed from the blood per unit time.

FIG. 39 shows a variation of this concept in which two (or more) series exposure units are arranged so that the blood stream is exposed to a greater amount for laser light per unit time. This increases the amount of carbon monoxide removed from the blood per unit time.

Figure 40:
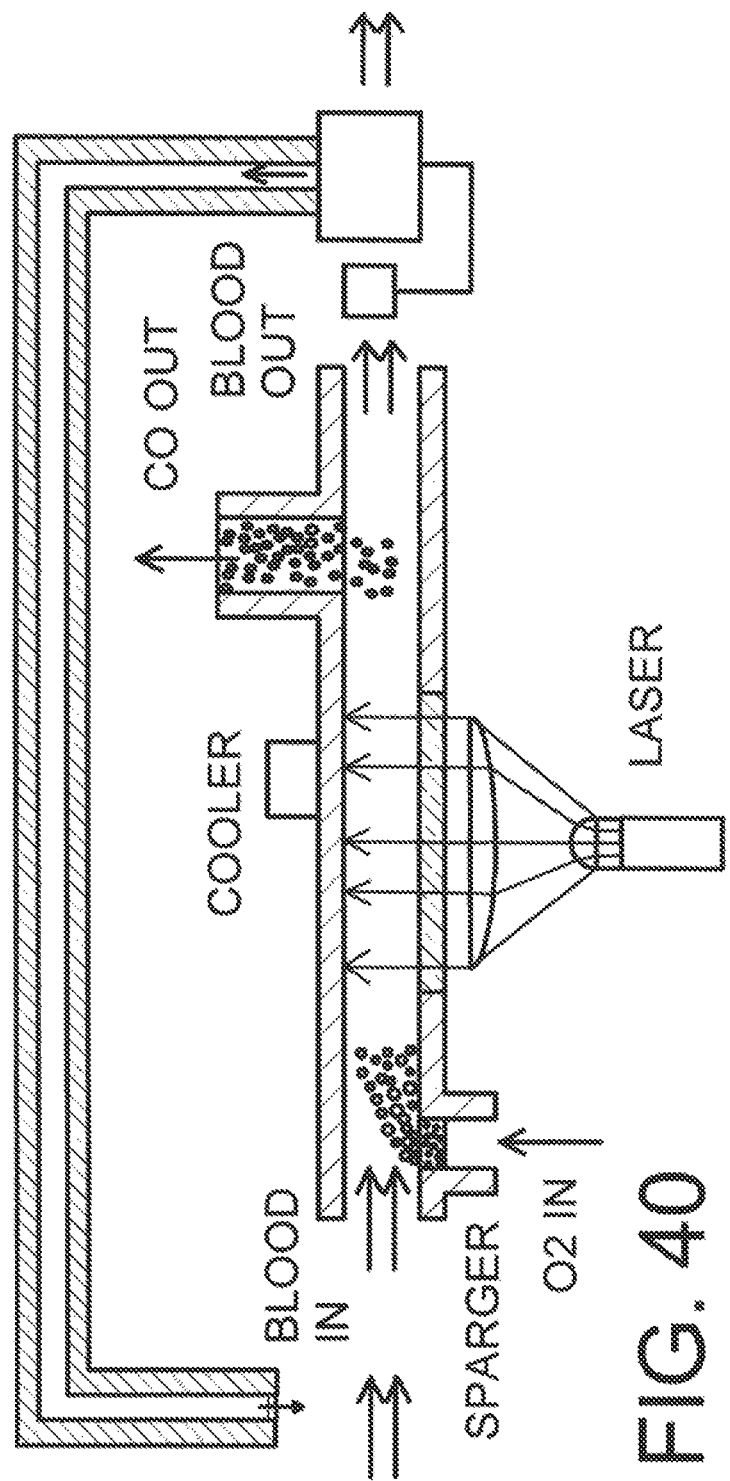
FIG. 40 shows a variation of the concept shown in FIG. 37, in which the exposure unit is provided with a feedback loop controlled by an output sensor that recycles blood back though the exposure zone if the level of carbon monoxide in the output blood is above the acceptable level. This arrangement assures that the blood is exposed to a sufficient amount for laser light to reduce the carbon monoxide to the desired level.

FIG. 40 shows a variation of this concept in which the exposure unit is provided with a feedback loop controled by an output sensor that recycles blood back though the exposure zone if the level of carbon monoxide in the output blood is above the exceptable level. This arrangement assures that the blood is exposed to a sufficient amount for laser light to reduce the carbon monoxide to the desired level.

Figure 13:
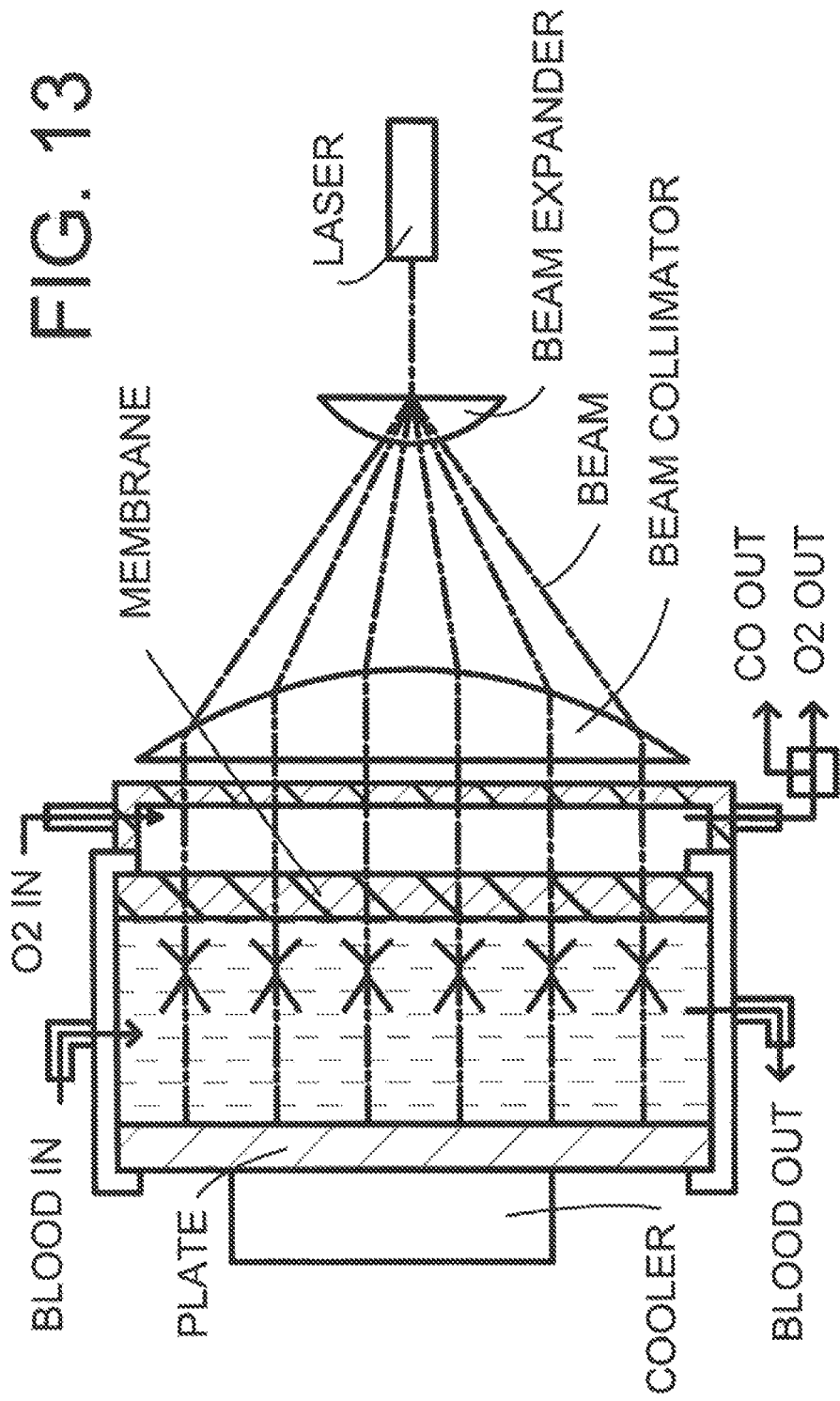
FIG. 13 shows a diagrammatic representation of an exposure cell embodying the principles of the present invention; presenting the basic design for an exposure cell that employs a gas-permeable light window.

FIG. 13 shows a diagrammatic representation of an exposure cell embodying some of the principles of the present invention; presenting the basic design for an exposure cell that employs a gas-permeable light window. Carbon monoxide poisoned blood is fed into and out of an exposure zone, through a gas-permeable window. Laser light of a effective frequency is sent though an oxygen and carbon-monoxide zone, and through a gas permeable window, into the blood. The light releases the carbon monoxide from the blood so that the carbon monoxide is replaced by oxygen. A cooler is provided on the thermally conductive back wall of the exposure zone to maintain the blood at the optimum temperature.

Figure 14:
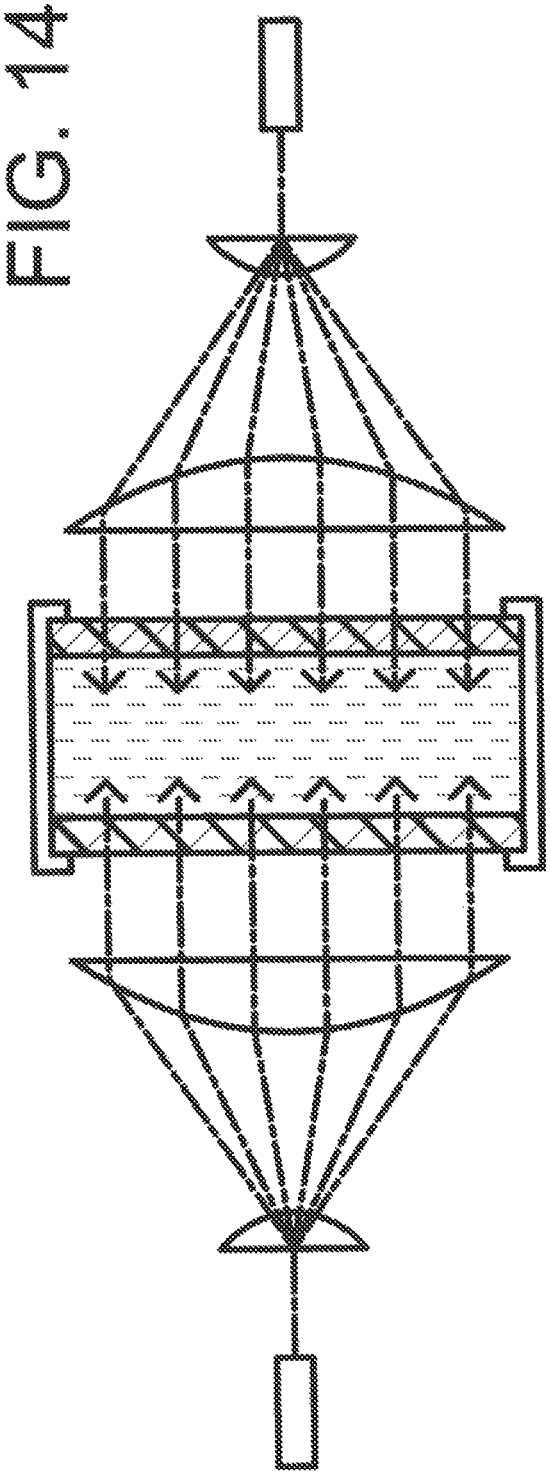
FIG. 14 shows a diagrammatic representation of an exposure cell embodying the principles of the present invention, presenting an exposure zone that receives the laser light from opposite sides from lasers on opposite sides.

FIG. 14 shows a diagrammatic representation of an exposure cell embodying some of the principles of the present invention, presenting an exposure zone that receives the laser light from opposite sides from lasers on opposite sides, in order to increase the amount of light per unit of time.

Figure 15:
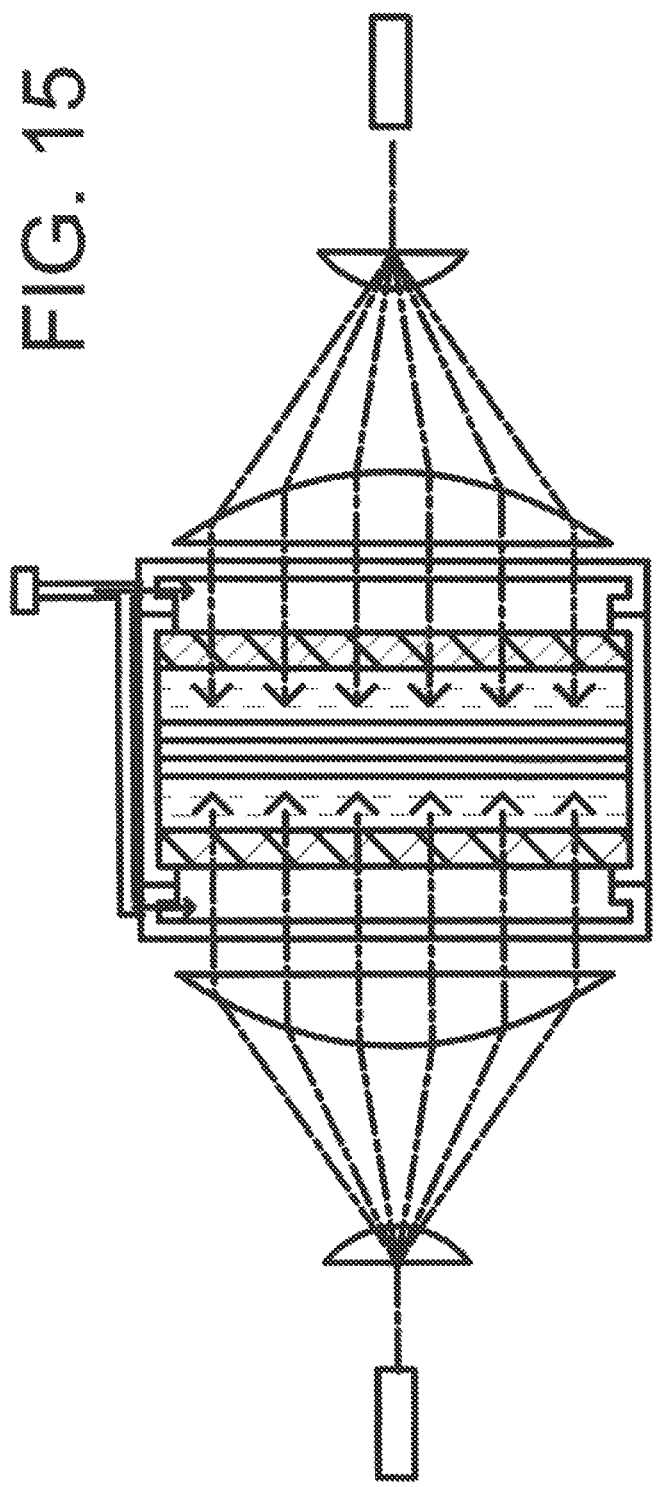
FIG. 15 shows a diagrammatic representation of an exposure cell embodying the principles of the present invention, presenting two adjacent exposure zones, each of which receives the laser light from separate lasers on opposite sides.

FIG. 15 shows a diagrammatic representation of an exposure cell embodying some of the principles of the present invention, presenting two adjacent back-to-back exposure zones, each as shown in FIG. 13, but each of which receives the laser light from separate lasers on opposite sides, in order to increase the amount of light per unit of time.

Figure 16:
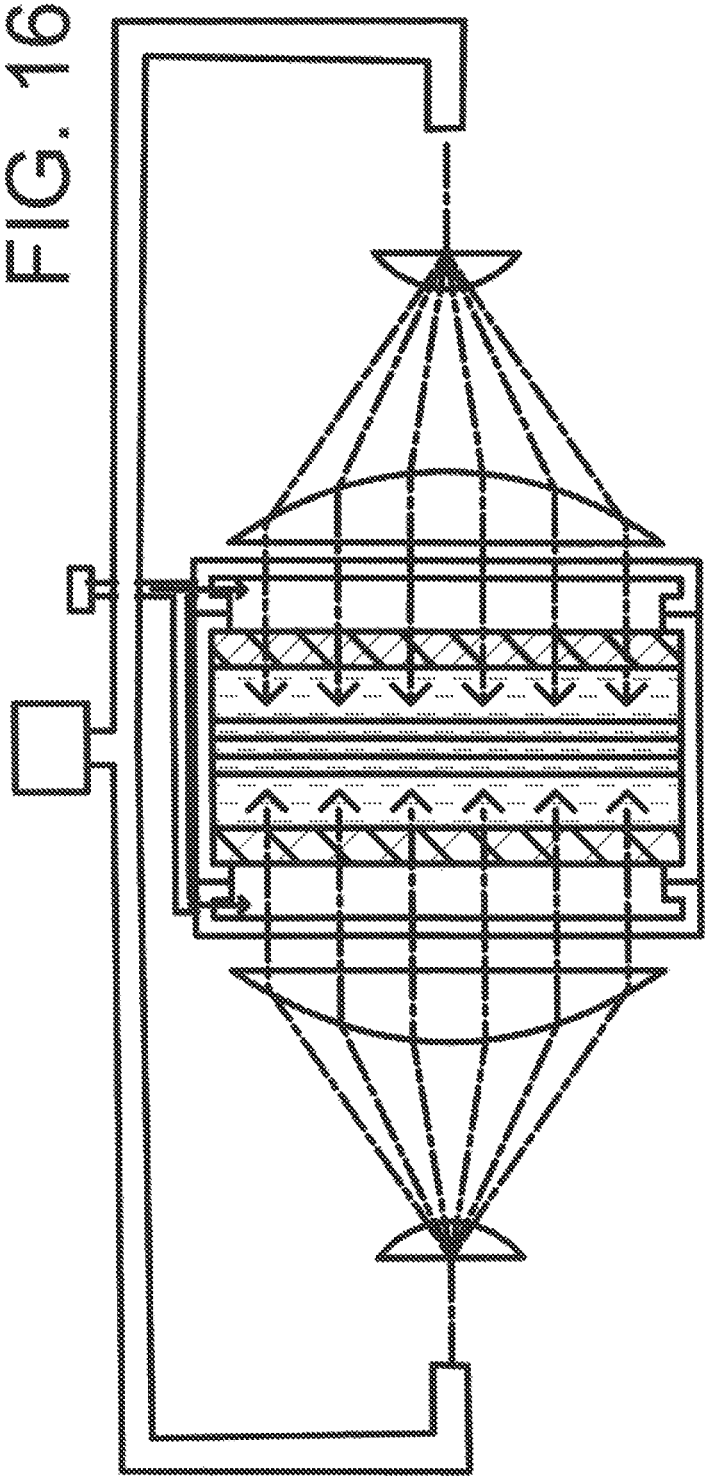
FIG. 16 shows a diagrammatic representation of an exposure cell embodying the principles of the present invention, presenting two adjacent exposure zones, each of which receives the laser light from a laser, that sends the light through fiberoptic light guides to opposite sides of the exposure cell.

FIG. 16 shows a diagrammatic representation of an exposure cell embodying some of the principles of the present invention, presenting two adjacent exposure zones, each of which receives the laser light from a laser, that sends the light through fiberoptic light guides to opposite sides of the exposure cell, in order to increase the amount of light per unit of time.

Figure 17:
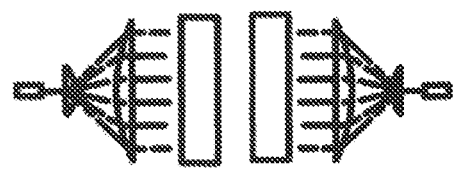
FIG. 17 shows a diagrammatic representation of an exposure cell embodying the principles of the present invention, presenting two adjacent exposure zones, each of which receives the laser light from separate lasers on opposite sides.

FIG. 17 shows a diagrammatic representation of an exposure cell embodying some of the principles of the present invention, presenting two adjacent back-to-back exposure zones, each of which receives the laser light from separate lasers on opposite sides, in order to increase the amount of light per unit of time.

Figure 18:
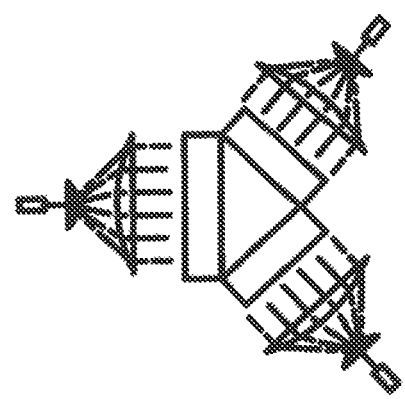
FIG. 18 shows a diagrammatic representation of an exposure cell embodying the principles of the present invention, presenting three adjacent exposure zones, each of which receives the laser light from separate lasers on opposite sides.

FIG. 18 shows a diagrammatic representation of an exposure cell embodying some of the principles of the present invention, presenting three adjacent back-to-center exposure zones, each of which receives the laser light from separate lasers on opposite sides, in order to increase the amount of light per unit of time.

Figure 19:
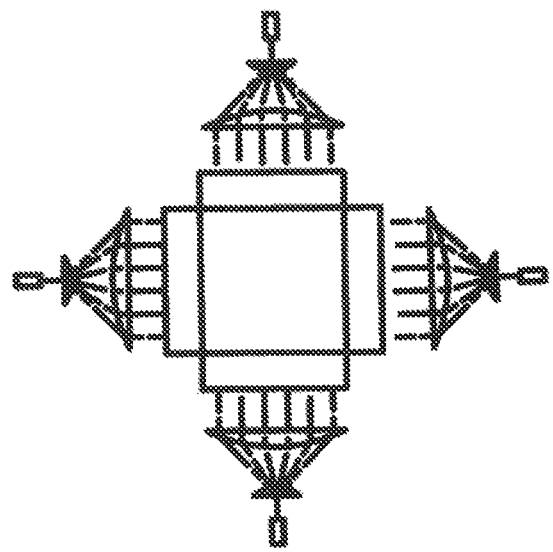
FIG. 19 shows a diagrammatic representation of an exposure cell embodying the principles of the present invention, presenting four adjacent exposure zones, each of which receives the laser light from separate lasers on opposite sides.

FIG. 19 shows a diagrammatic representation of an exposure cell embodying some of the principles of the present invention, presenting four adjacent back-to-center exposure zones, each of which receives the laser light from separate lasers on opposite sides, in order to increase the amount of light per unit of time.

Figure 20:
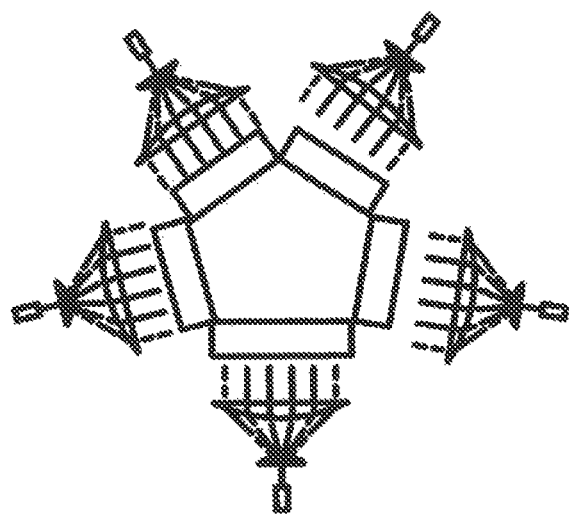
FIG. 20 shows a diagrammatic representation of an exposure cell embodying the principles of the present invention, presenting five adjacent exposure zones, each of which receives the laser light from separate lasers on opposite sides.

FIG. 20 shows a diagrammatic representation of an exposure cell embodying some of the principles of the present invention, presenting five adjacent back-to-center exposure zones, each of which receives the laser light from separate lasers on opposite sides, in order to increase the amount of light per unit of time.

Figure 21:
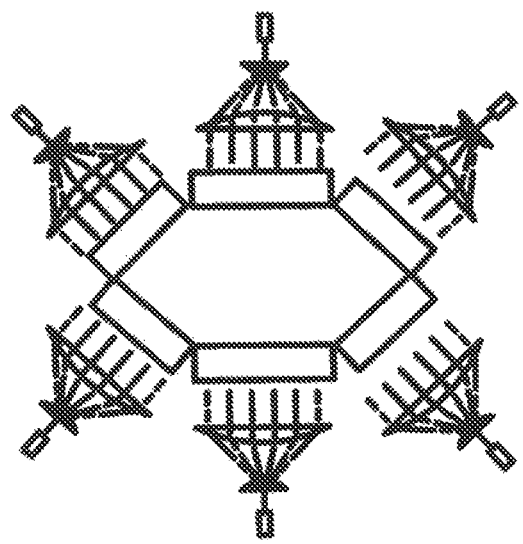
FIG. 21 shows a diagrammatic representation of an exposure cell embodying the principles of the present invention, presenting six adjacent exposure zones, each of which receives the laser light from separate lasers on opposite sides.

FIG. 21 shows a diagrammatic representation of an exposure cell embodying some of the principles of the present invention, presenting six adjacent back-to-center exposure zones, each of which receives the laser light from separate lasers on opposite sides, in order to increase the amount of light per unit of time.

Figure 22:
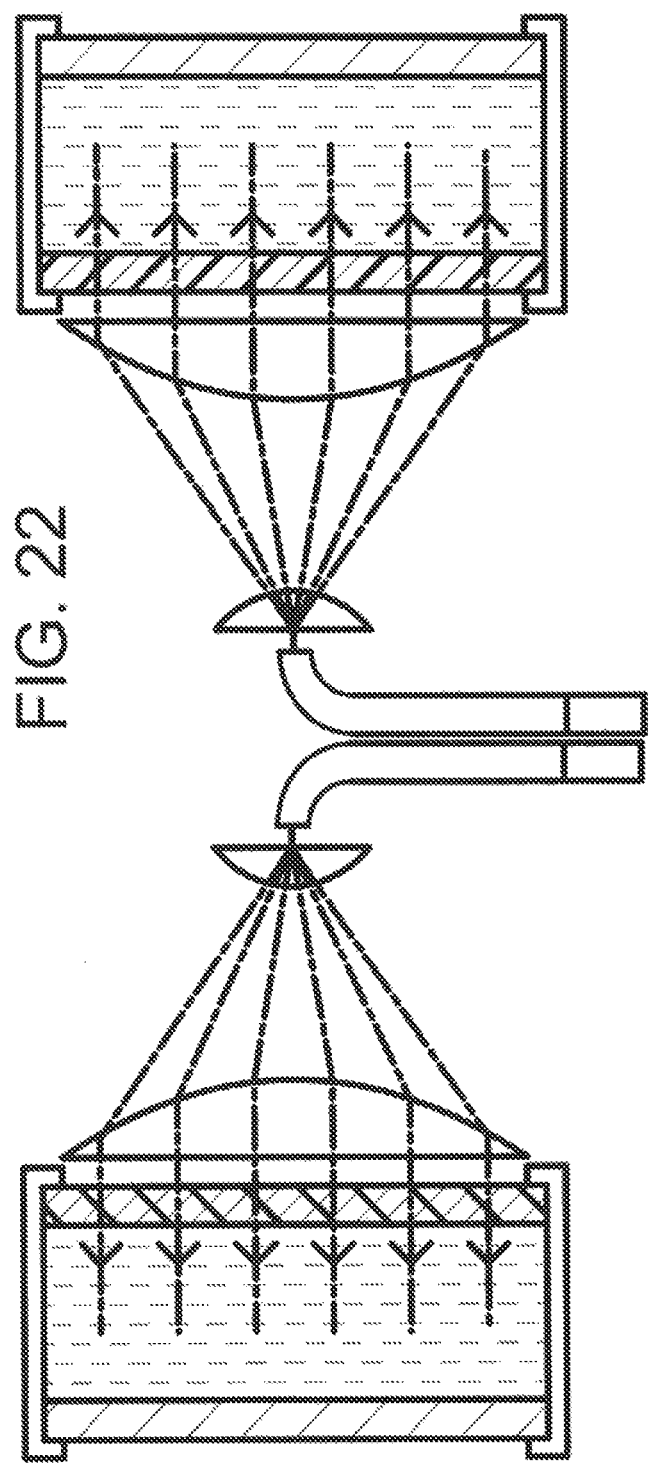
FIG. 22 shows a diagrammatic representation of an exposure cell embodying the principles of the present invention, presenting two adjacent exposure zones, with facing light windows, each of which receives the laser light from the end of light guides between the windows, essentially providing an internal light source within the exposure cell structure.

FIG. 22 shows a diagrammatic representation of an exposure cell embodying some of the principles of the present invention, presenting two adjacent exposure zones, with facing light windows, each of which receives the laser light from the end of light guides between the windows, essentially providing an internal light source within the exposure cell structure, in order to increase the amount of light per unit of time.

Figure 23:
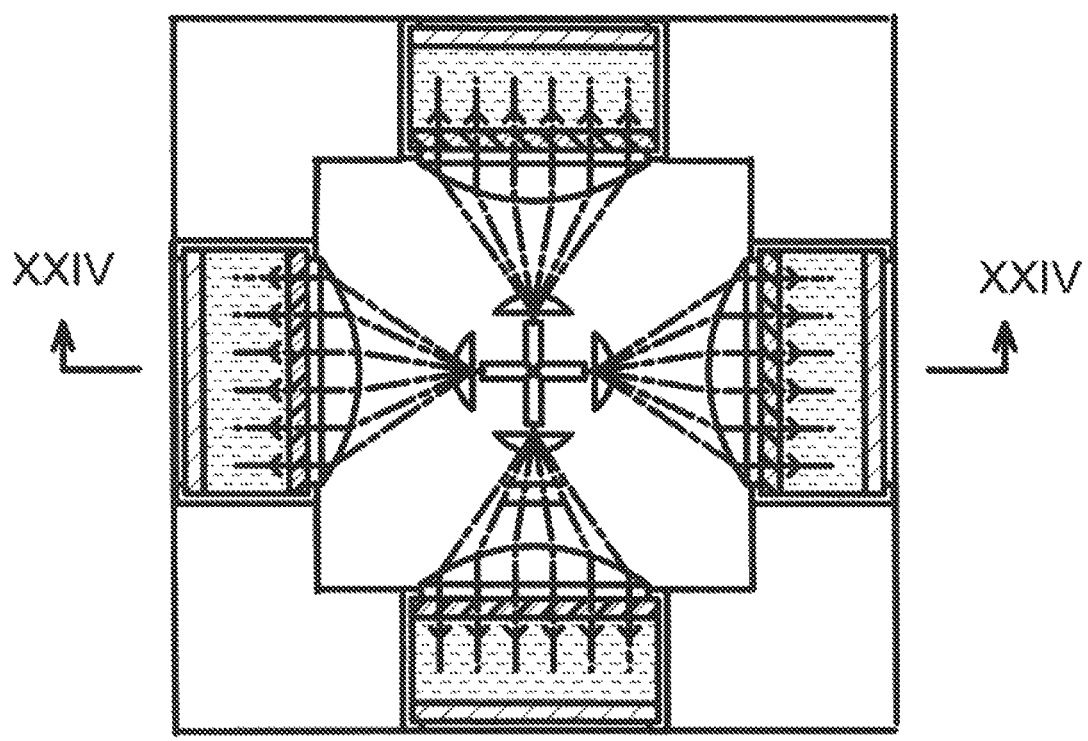
FIG. 23 shows a diagrammatic representation of an exposure cell embodying the principles of the present invention, presenting an top view of four adjacent exposure zones, with facing light windows, each of which receives the laser light from the end of light guides between the windows, essentially providing an internal light source within the exposure cell structure.

FIG. 23 shows a diagrammatic representation of an exposure cell embodying some of the principles of the present invention, presenting an top view of four adjacent exposure zones, with facing light windows, each of which receives the laser light from the end of light guides between the windows, essentially providing an internal light source within the exposure cell structure, in order to increase the amount of light per unit of time.

Figure 24:
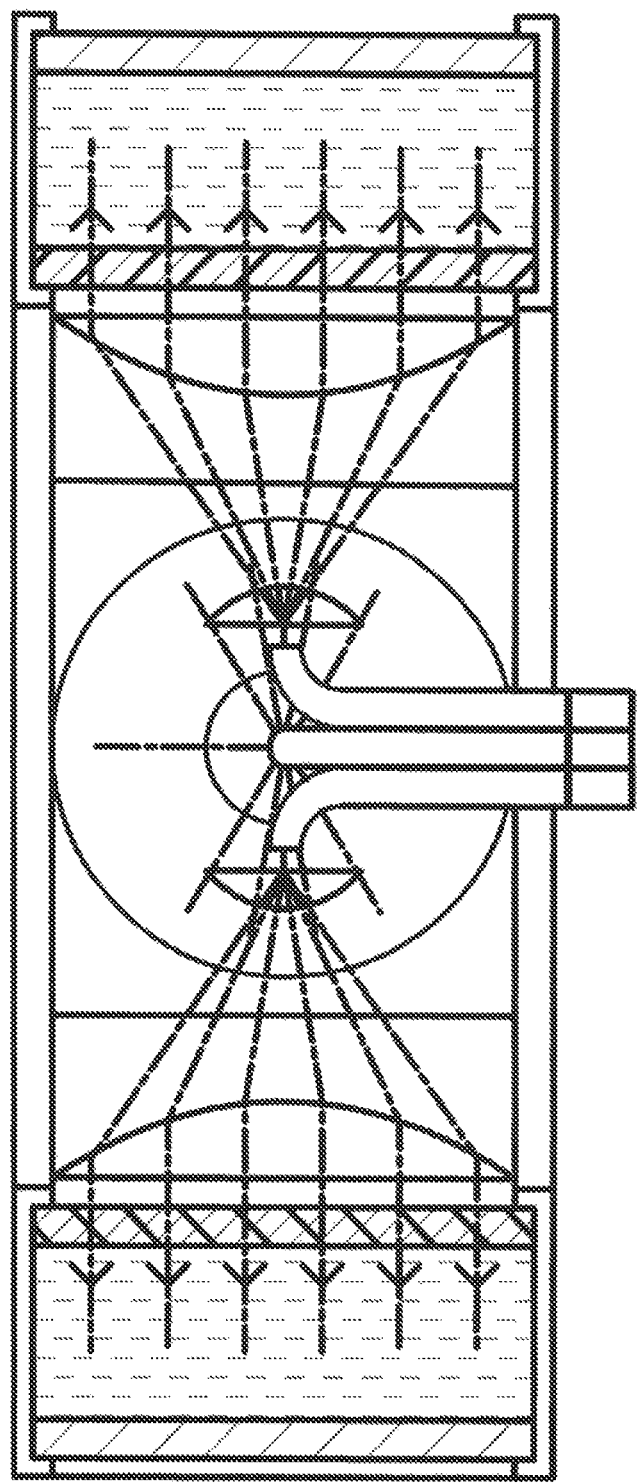
FIG. 24 shows a diagrammatic representation of an exposure cell embodying the principles of the present invention, presenting an sectional elevation view taken along line XXIV-XXIV of FIG. 23, of four adjacent exposure zones.

FIG. 24 shows a diagrammatic representation of an exposure cell embodying some of the principles of the present invention, presenting an sectional elevation view taken along line XXIV-XXIV of FIG. 23, of four adjacent exposure zones, with facing light windows, each of which receives the laser light from the end of light guides between the windows, essentially providing an internal light source within the exposure cell structure, in order to increase the amount of light per unit of time.

FIG. 25 shows a diagrammatic representation of an exposure cell embodying some of the principles of the present invention, presenting the top view of a exposure cell including four adjacent exposure zones as shown in FIG. 19, each of which receives the laser light from separate external lasers on four opposite sides, in order to increase the amount of light per unit of time. The drawing shows input lines for gas in, blood in, and coolant in, that feed into a upper manifold. A lower manifold would be the mirror image of the upper manifold. If the light is provided internally, such as in FIG. 23, with the light window facing the inside, than the order of the input lines is reversed.

FIG. 26 shows a diagrammatic representation of an exposure cell embodying some of the principles of the present invention, presenting the front elevation view of a exposure cell including four adjacent exposure zones as shown in FIG. 19, each of which receives the laser light from separate external lasers on four opposite sides, in order to increase the amount of light per unit of time. The drawing shows input lines for gas in, blood in, and coolant in, that feed into a upper manifold. The lower manifold would be the mirror image of the upper manifold, and shows the gas out, blood out, and coolant out output lines. If the light is provided internally, such as in FIG. 23, with the light windows facing inward, than the order of the input lines and output lines are reversed.

Figure 27:
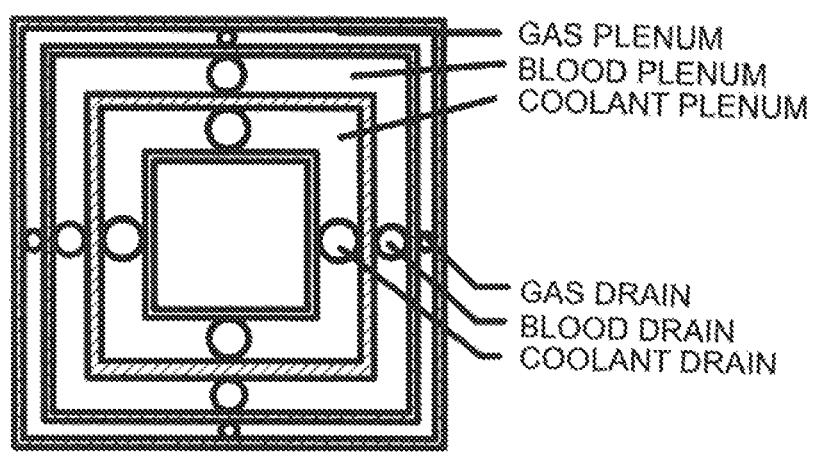
FIG. 27 shows a diagrammatic representation of an exposure cell embodying the principles of the present invention, presenting a section plan view of FIG. 26, taken along line XXVII-XXVII in FIG. 26.

FIG. 27 shows a diagrammatic representation of an exposure cell embodying some of the principles of the present invention, presenting a section top view of FIG. 26, taken along line XXVII-XXVII in FIG. 26. It shows the inside of the distribution manifold that includes a gas plenum, a blood plenum, and a coolant plenum. Each plenum has drains that feed their respective fluids into the respective exposure zone layers of the four zones. A lower manifold would be the mirror image of the upper manifold. If the light is provided internally, such as in FIG. 23, than the order of the plenums would be reversed, with the gas plenum on the inside, and the coolant plenum on the outside.

Figure 28:
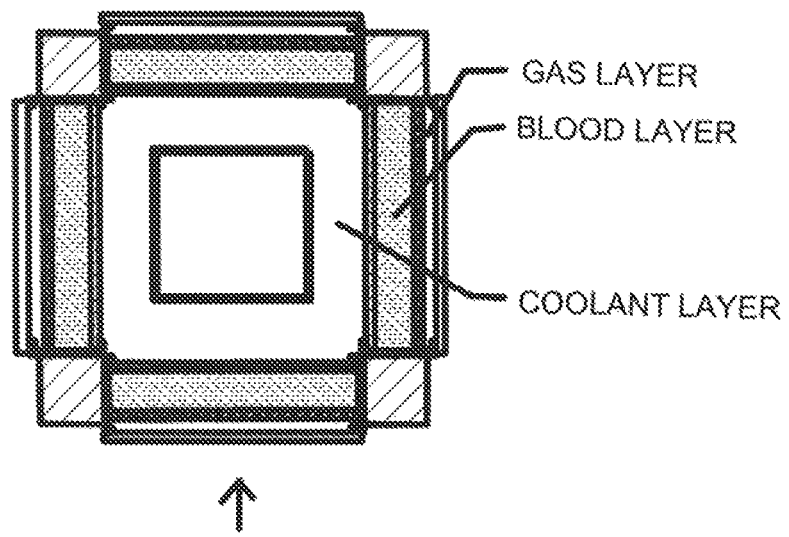
FIG. 28 shows a diagrammatic representation of an exposure cell embodying the principles of the present invention, presenting a section plan view of FIG. 26, taken along line XXVIII-XXVIII in FIG. 26.

FIG. 28 shows a diagrammatic representation of an exposure cell embodying some of the principles of the present invention, presenting a section plan view of FIG. 26, taken along line XXVIII-XXVIII in FIG. 26. It shows the inside of the exposure zones that includes a gas layer inside, a blood layer in the middle, and a coolant layer outside. Each plenum in the upper manifold drains their respective fluids into the respective exposure zone layer. A lower manifold would be the mirror image of the upper manifold, and would have plenums that receive fluid from the respective layers. If the light is provided internally, such as in FIG. 23, than the order of the plenums would be reversed, gas layer outside, a blood layer in the middle, and a coolant layer inside.

Figure 29:
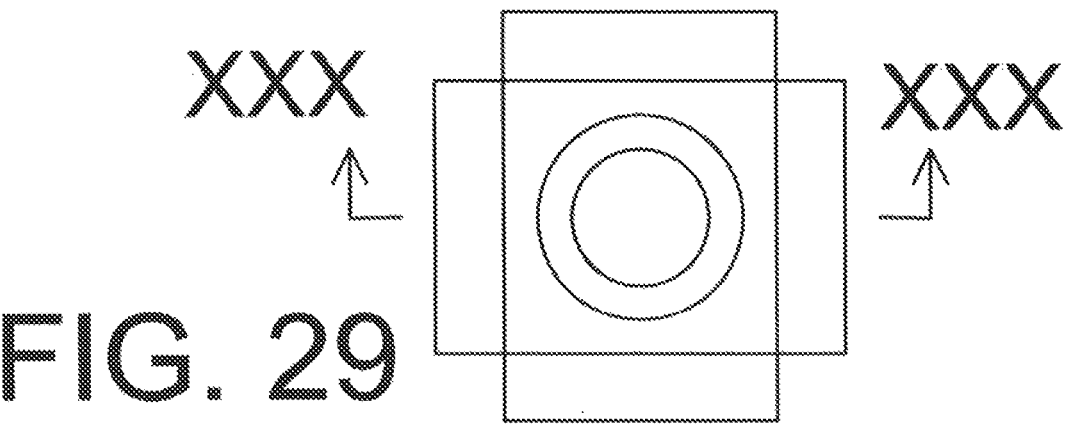
FIG. 29 shows a diagrammatic representation of an exposure cell embodying the principles of the present invention, presenting a top view of a internal laser light source that provides laser light to a surrounding ring of four inwardly facing exposure zones.

FIG. 29 shows a diagrammatic representation of an exposure cell embodying some of the principles of the present invention, presenting a top view of a internal laser light source that provides laser light to a surrounding ring of four inwardly facing exposure zones.

Figure 30:
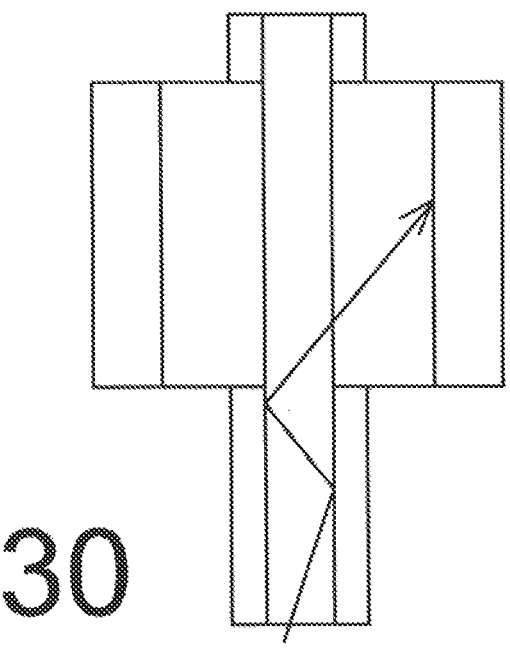
FIG. 30 shows a diagrammatic representation of an exposure cell embodying the principles of the present invention, presenting a sectional front elevation view along line XXX-XXX of FIG. 29.

FIG. 30 shows a diagrammatic representation of an exposure cell embodying some of the principles of the present invention, presenting a sectional front elevation view along line XXX-XXX of FIG. 29. Ordinarily, the light in a light guide would be maintained within the light guide by a reflective cladding on the outside of the light guide. In this case, the cladding is removed from the portion of the light guide that is within the inner cavity of the four exposure cells, so that light leaks out of the wave guide and enters the inward facing windows of the four exposure cells.

FIG. 31 shows a diagrammatic representation of an exposure cell embodying some of the principles of the present invention, presenting a top view of a internal laser light source that provides laser light to the inward facing window of a surrounding ring of a cylindrical exposure zone.

FIG. 32 shows a diagrammatic representation of an exposure cell embodying some of the principles of the present invention, presenting a sectional front elevation view along line XXXII-XXXII of FIG. 31. Ordinarily, the light in a light guide would be maintained within the light guide by a reflective cladding on the outside of the light guide. In this case, the cladding is removed from the portion of the light guide that is within the inner cavity of the cylindrical exposure cell, so that light leaks out of the wave guide and enters the inward facing window of the cylindrical exposure cell.

Figure 33:
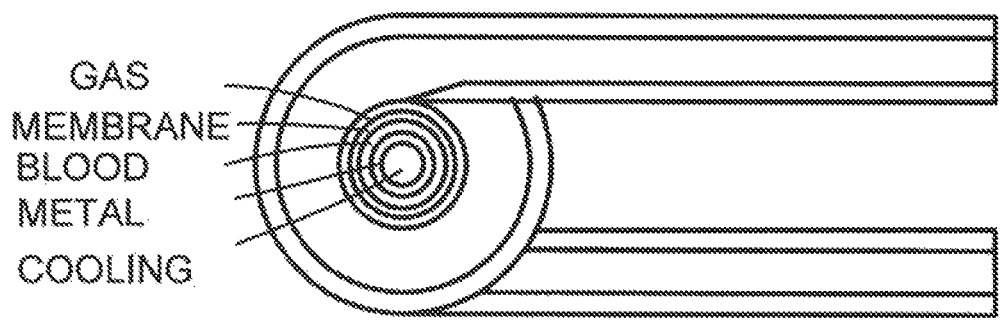
FIG. 33 shows a diagrammatic representation of an exposure cell embodying the principles of the present invention, presenting a top view of a coiled external laser light source that provides laser light to the outward facing window of a cylindrical exposure zone.

FIG. 33 shows a diagrammatic representation of an exposure cell embodying some of the principles of the present invention, presenting a top view of a coiled external laser light source that provides laser light to the outward facing window of a cylindrical exposure zone. Ordinarily, the light in a light guide would be maintained within the light guide by a reflective cladding on the outside of the light guide. In this case, the cladding is removed from the inside of the portion of the light guide that is wrapped around a cylindrical exposure cell, so that light leaks out of the inside facing surface of the wave guide and enters the outward facing window of the cylindrical exposure cell.

Figure 34:
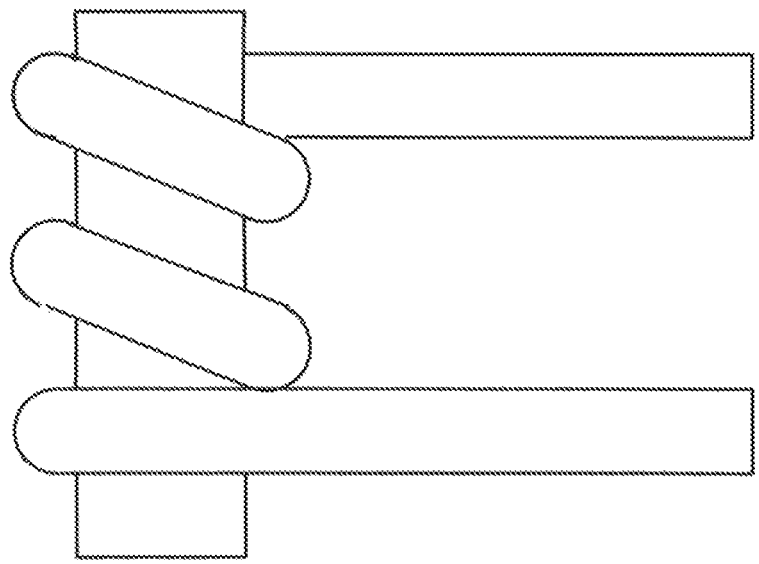
FIG. 34 shows a diagrammatic representation of an exposure cell embodying the principles of the present invention, presenting a front elevation view of the structure of FIG. 33

FIG. 34 shows a diagrammatic representation of an exposure cell embodying some of the principles of the present invention, presenting a front elevation view of the structure of FIG. 33.

Figure 35:
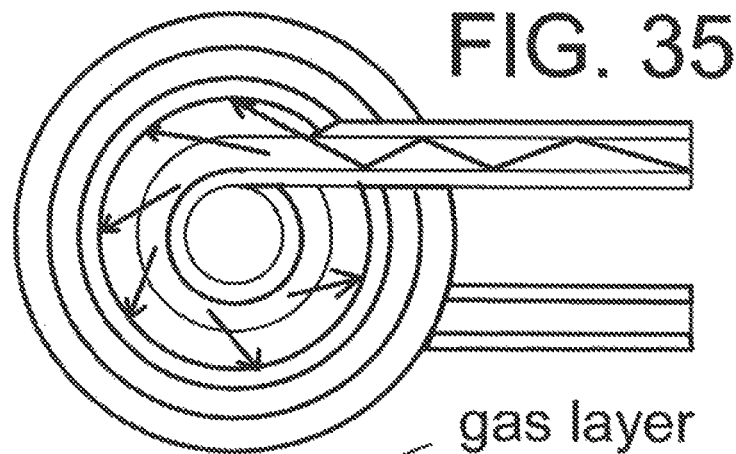
FIG. 35 shows a diagrammatic representation of an exposure cell embodying the principles of the present invention, presenting a top view of a coiled internal laser light source that provides laser light to the inward facing window of a cylindrical exposure zone.

FIG. 35 shows a diagrammatic representation of an exposure cell embodying some of the principles of the present invention, presenting a top view of a coiled internal laser light source that provides laser light to the inward facing window of a cylindrical exposure zone. Ordinarily, the light in a light guide would be maintained within the light guide by a reflective cladding on the outside of the light guide. In this case, the cladding is removed from the outward facing side of the portion of the light guide that is wrapped around a cylindrical exposure cell, so that light leaks out of the outside surface of the wave guide and enters the inward facing window of the cylindrical exposure cell.

Figure 36:
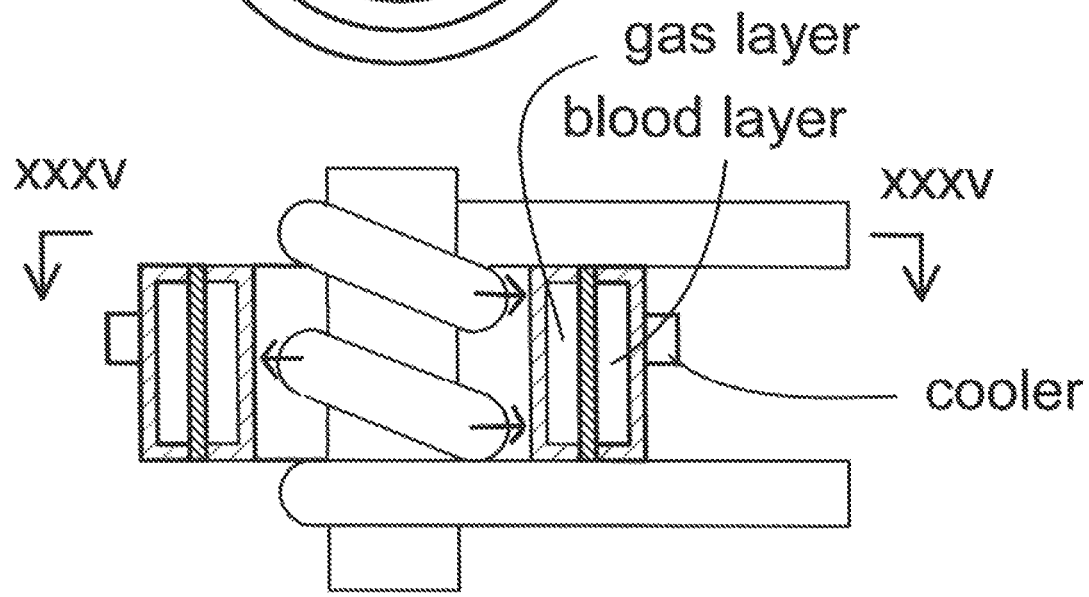
FIG. 36 shows a diagrammatic representation of an exposure cell embodying the principles of the present invention, presenting a front elevation view, in partial section, of the structure of FIG. 35.

FIG. 36 shows a diagrammatic representation of an exposure cell embodying some of the principles of the present invention, presenting a front elevation view, in partial section, of the structure of FIG. 35.

FIG. 37 shows a diagrammatic representation of an alternative exposure cell embodying some of the principles of the present invention, in which the light window is not gas permeable. Instead of using a gas-permeable membrane, the poisoned blood could have the disassociated carbon monoxide extracted, by bubbling oxygen through the poisoned blood, exposing the poisoned blood to the laser light, and then harvesting the resulting bubbles of carbon monoxide.

The use of a gas permeable membrane to allow the oxygen into the blood and the carbon monoxide out of the blood is a desirable approach, but another approach would use a gas impermeable laser light window, with oxygen bubbled into the blood upstream of the laser exposure zone, and the carbon monoxide bubbled out of the blood downstream of the laser exposure zone. FIG. 37 shows an embodiment of such a concept.

This embodiment of the exposure cell 500 has a laser exposure zone 502, through which a stream of blood 506 passes. The laser exposure zone 502 is defined by a wall 504. The blood stream 506 is extracted from the body of the carbon-monoxide-poisoned person and is returned to the body of the carbon-monoxide-poisoned person, after the blood is treated.

The basic version of this exposure cell, as shown in FIG. 37, has a laser exposure zone 502 with a laser 508 shining appropriate light 510 into the zone 502 through laser transparent, but gas-impermeable window 512, in the wall 504.

Upstream of the exposure cell 500, an oxygen stream 514 is injected into the blood stream 506 through a sparger 516 that breaks the oxygen stream 514 into tiny oxygen bubbles 518 from which the oxygen is quickly dissolved into the blood.

Downstream of the exposure cell 500, an carbon monoxide stream 520 is formed when carbon monoxide is released from the blood stream 506 through a separator 522 that separates the carbon monoxide from the blood, for example, by allowing carbon monoxide to pass through a perforated separator plate, while not allowing the blood to pass through the plate.

A cooler 524 cools the wall 504 of the exposure cell 502, and thereby the blood in the cell, to keep the blood at the optimum temperature.

FIG. 38 shows a variation of the concept shown in FIG. 37, in which two (or more) parallel exposure units are arranged so that the blood stream is exposed to a greater amount for laser light per unit time. This increases the amount of carbon monoxide removed from the blood per unit time.

FIG. 39 shows a variation of the concept shown in FIG. 37, in which two (or more) series exposure units are arranged so that the blood stream is exposed to a greater amount for laser light per unit time. This increases the amount of carbon monoxide removed from the blood per unit time.

FIG. 40 shows a variation of the concept shown in FIG. 37, in which the exposure unit is provided with a feedback loop controlled by an output sensor that recycles blood back though the exposure zone if the level of carbon monoxide in the output blood is above the acceptable level. This arrangement assures that the blood is exposed to a sufficient amount for laser light to reduce the carbon monoxide to the desired level.

FIG. 41 shows a diagrammatic representation of an exposure cell embodying some of the principles of the present invention; presenting the basic design, shown in FIG. 13, for an exposure cell that employs a gas-permeable light window. FIG. 41 includes a system for minimizing the distension of the membrane that forms the gas-permeable light window. Often the membrane is not rigid, but it is desirable to keep it flat. One way to do that is to balance the forces in each side of the membrane so that the membrane stays flat, by increasing the force on the distended side until it flattens. In this embodiment, the location is the center of the membrane is monitored, and the force on the gas side of the membrane is adjusted to flatten the membrane and balance the force presented to the blood side of the membrane by the blood when it is flat.

In FIG. 41, the membrane flattening function is conducted as follows. A membrane distance sensor, mounted on the outside wall of the gas layer, uses a distance light beam to monitor the distance between fixed membrane distance sensor and the center of the membrane. The membrane distance sensor sends the distance signal though a wire to a computer and flow controller, and uses the distance signal to control the flow of gas out of the gas layer, and, thereby, the pressure in the gas layer, and thereby, the force of the gas on the membrane.

The computer is programmed to keep the membrane flat. When the distance between the membrane and the membrane distance sensor changes from the flat membrane condition, the computer adjusts the flow of gas out of the gas layer, and thereby, the force of the gas on the membrane, to return the membrane to the flat condition.

It is obvious that minor changes may be made in the form and construction of the invention without departing from the material spirit thereof. It is not, however, desired to confine the invention to the exact form herein shown and described, but it is desired to include all such as properly come within the scope claimed.

The invention having been thus described, what is claimed as new and desire to secure by Letters Patent is:

1. A system for treatment of carbon monoxide poisoning of the blood of a living victim, comprising:
   a. an exposure cell having an oxygen supply,
   b. a first sub-system adapted to remove a portion of the blood from the victim according to a blood flow rate and to place the portion in the exposure cell,
   c. a second sub-system adapted to expose the portion in the cell to dissociative light that causes dissociation of carbon monoxide from hemoglobin, the dissociative light defined by a laser having a wattage based on the blood flow rate of the first sub-system and a treatment time for restoring a percentage of hemoglobin-bound oxygen in the blood, and
   d. a third sub-system adapted to return the portion to the victim as a timely countermeasure to the CO poisoning while maintaining a temperature of the blood in a physiological range upon return to the victim.

2. The system as recited in claim 1, wherein the dissociative light is of a wave length selected from the group of 540 and 570 nanometers and combinations thereof.

3. The system as recited in claim 1, wherein the dissociative light is of an intensity of at least 9.5 Joules per milliliter of blood.

4. The system as recited in claim 1, wherein the dissociative light is of an intensity of at least 9.5 Watts per milliliter of blood flow per second.

5. The system as recited in claim 1, wherein the first and third sub-systems are a concentric double lumen cannula.

6. The system as recited in claim 1, wherein the system includes a subsystem that captures and isolates the disassociated carbon monoxide.

7. The system of claim 1, wherein the laser is adapted for mitigating an overheating of blood from a high wattage of the dissociative light.

8. The system of claim 1, further comprising a gaseous oxygen supply and a membrane responsive to the gaseous oxygen supply for transporting and combining the oxygen with hemoglobin.

9. The system of claim 8, wherein the membrane is a semipermeable membrane of a thickness to facilitate the displacement and release of CO following its photodissociation from carboxyhemoglobin, replacement with oxygen and subsequent transmission and removal of the CO.

10. The method for treatment of carbon monoxide poisoning of a Livonia victim, comprising the steps of:
    a. removing a portion of the blood from the victim and placing the portion in an exposure cell having an oxygen supply,
    b. exposing the portion in the cell to dissociative light that causes dissociation of carbon monoxide from hemoglobin according to a blood flow rate, the dissociative light defined by a laser having a wattage based on the blood flow rate of the first sub-system and a treatment time for restoring a percentage of hemoglobin-bound oxygen in the blood, and
    c. returning the portion to the victim as a timely countermeasure to CO poisoning while maintaining a temperature of the blood in a physiologic range upon return to the victim.

11. The method as recited in claim 10, wherein the dissociative light is of a wave length selected from the group of 540 and 570 nanometers and combinations thereof.

12. The method as recited in claim 10, wherein the dissociative light is of a intensity of at least 9.5 Joules per milliliter of blood.

13. The method as recited in claim 10, wherein the dissociative light is of a intensity of at least 9.5 Watts per milliliter of blood flow per second.

14. The method as recited in claim 10, wherein the portion of the blood is removed from and returned to the living victim using a concentric double lumen cannula.

15. The method as recited in claim 10, wherein the method includes an injection of oxygen into the cell.

16. The method as recited in claim 10, wherein the method includes capturing and isolating the disassociated carbon monoxide.

17. A system for treatment of carbon monoxide poisoning of the blood of a living creature, comprising a first sub-system having an oxygen supply and adapted to cause dissociation of carbon monoxide from hemoglobin according to a blood flow rate, and a second sub-system adapted to capture and isolate the dissociated carbon monoxide responsive to dissociative light defined by a laser having a wattage based on the blood flow rate of the first sub-system and a treatment time for restoring a percentage of hemoglobin-bound oxygen in the blood as a timely countermeasure to CO poisoning while maintaining a temperature of the blood in a physiologic range upon return to the living creature.

* * * * *